(12) United States Patent
Singh et al.

(10) Patent No.: US 11,293,915 B2
(45) Date of Patent: Apr. 5, 2022

(54) BIO-ADHESIVE GELS AND METHODS OF USE

(71) Applicant: Cornell University, Ithaca, NY (US)

(72) Inventors: Ankur Singh, Ithaca, NY (US); Ravi G. Patel, Livingston, NJ (US)

(73) Assignee: CORNELL UNIVERSITY, Ithaca, NY (US)

( * ) Notice: Subject to any disclaimer, the term of this patent is extended or adjusted under 35 U.S.C. 154(b) by 344 days.

(21) Appl. No.: 15/309,276

(22) PCT Filed: May 8, 2015

(86) PCT No.: PCT/US2015/029972
§ 371 (c)(1),
(2) Date: Nov. 7, 2016

(87) PCT Pub. No.: WO2015/172073
PCT Pub. Date: Nov. 12, 2015

(65) Prior Publication Data
US 2017/0074861 A1    Mar. 16, 2017

Related U.S. Application Data

(60) Provisional application No. 61/990,280, filed on May 8, 2014.

(51) Int. Cl.
*G01N 33/50* (2006.01)
*C12N 5/00* (2006.01)

(52) U.S. Cl.
CPC ....... *G01N 33/5011* (2013.01); *C12N 5/0012* (2013.01); *C12N 5/0062* (2013.01); *C12N 2533/10* (2013.01); *C12N 2533/30* (2013.01); *C12N 2533/54* (2013.01)

(58) Field of Classification Search
CPC ............ C12N 2533/30; C12N 2533/54; C12N 5/0012; C12N 5/0062
See application file for complete search history.

(56) References Cited

U.S. PATENT DOCUMENTS

| | | | |
|---|---|---|---|
| 7,056,901 | B2 | 6/2006 | Frechet et al. |
| 7,226,617 | B2 | 6/2007 | Ding et al. |
| 7,449,180 | B2 | 11/2008 | Kisiday et al. |
| 2011/0275572 | A1 | 11/2011 | Rafailovich et al. |
| 2012/0078296 | A1 | 3/2012 | Lee et al. |
| 2012/0225101 | A1* | 9/2012 | Kao .......................... C08L 5/08 424/400 |
| 2014/0086975 | A1* | 3/2014 | Sinko ..................... A61K 31/65 424/429 |
| 2014/0271843 | A1 | 9/2014 | Ma et al. |
| 2014/0341842 | A1 | 11/2014 | Zarembinski et al. |
| 2015/0004205 | A1 | 1/2015 | Elbert et al. |
| 2015/0071997 | A1 | 3/2015 | Garcia et al. |

FOREIGN PATENT DOCUMENTS

| | | |
|---|---|---|
| WO | 2007044515 | 4/2007 |
| WO | 2008098109 | 12/2008 |
| WO | 2012162345 | 11/2012 |
| WO | 2014028209 | 2/2014 |
| WO | 2014039245 | 3/2014 |
| WO | 2014180970 | 11/2014 |

OTHER PUBLICATIONS

Xu et al., Redox-responsive targeted gelatin nanoparticles for delivery of combination wt-p53 expressing plasmid DNA and gemcitabine in the treatment of pancreatic cancer., BMC Cancer, vol. 14, p. 1-12 (Year: 2014).*
Gaharwar et al., Photocrosslinked nanocomposite hydrogels from PEG and silica nanospheres: Structural, mechanical and cell adhesion characteristics, Materials Science and Engineering, C 33, p. 1800-1807. (Year: 2013).*
Headen et al., Microfluidic-based generation of size-controlled, biofunctionalized synthetic polymer microgels for cell encapsulation, Advanced Materials, vol. 26, p. 3003-3008. (Year: 2014).*
Phelps et al, Maelimide cross-linked bioactive PEG hydrogel exhibits improved reaction kinetics and cross-liking for cell encapsulation and in-situ delivery, vol. 24, p. 1-12. (Year: 2013).*
Fu et al., 3D cell entrapment in crosslinked thiolated gelatin-poly(ethylene glycol) diacrylate hydrogels , Biomaterials, vol. 33, p. 48-58. (Year: 2012).*
Chung et al, Macrophage matrix metalloproteinase–2/–9 gene and protein expression following adhesion to ECM-derived multifunctional matrices via integrin complexation, vol. 28, p. 285-298. (Year: 2007).*
Zhang et al., "Micro- and nanogels with labile crosslinks—from synthesis to biomedical applications". Chem. Soc. Rev., 2015, 44, 1948-1973.
Patel et al., "Microscale Bioadhesive Hydrogel Arrays for Cell Engineering Applications". Cell Mol. Bioeng. Sep. 1, 2014;7(3):394-408.

(Continued)

*Primary Examiner* — Renee Claytor
*Assistant Examiner* — Tiffany M Gough
(74) *Attorney, Agent, or Firm* — Troutman Pepper Hamilton Sanders LLP

(57) ABSTRACT

A gel composition that forms a three dimensional gel microenvironment that is formed of an adhesive protein, a maleimide-functionalized poly alkylene oxide, a linking agent and a nanoparticle, the components forming an interpenetrating network that exhibits improved mechanical and biochemical properties, as well as creates a favorable microenvironment for cellular growth and proliferation. The gel composition also creates a favorable microenvironment for testing various agents on normal or diseased cells, including chemotherapeutic agents on cancer cells or other diseased cells.

15 Claims, 9 Drawing Sheets

(56) References Cited

OTHER PUBLICATIONS

Gaharwar et al., "Bioactive silicate nanoplatelets for osteogenic differentiation of human mesenchymal stem cells". Adv. Mater. 25(24):3329-3336, 2013.
International Search Report and Written Opinion for corresponding Application No. PCT/US 2015/029972 (dated Sep. 15, 2015).
International Preliminary Report on Patentability for corresponding Application No. PCT/US 2015/029972 (dated Nov. 8, 2016).

* cited by examiner

BIO-ADHESIVE GELS AND METHODS OF USE

CROSS REFERENCE TO RELATED PATENTS

This application claims the benefit of U.S. Provisional Patent Application No. 61/990,280 filed May 8, 2014, which is incorporated by reference.

STATEMENT REGARDING FEDERALLY-SPONSORED RESEARCH OR DEVELOPMENT

This invention was made with government support under 1R21CA185236-01 awarded by The National Institutes of Health. The government has certain rights in the invention.

FIELD OF THE INVENTION

The present disclosure relates generally to gel compositions that provide a three dimensional microenvironment of interpenetrating networks for culturing cells and testing the efficacy of drugs on various types of cells encapsulated therein.

BACKGROUND OF THE INVENTION

Gel compositions such as hydrogels and microgels are networks of polymer chains that are generally comprised of hydrophilic and highly absorbent natural or synthetic polymeric networks. Such compositions possess a degree of flexibility due in part to their similarity to natural tissue and because of their significant water content. These compositions are therefore useful in many biomedical and research applications.

Cell encapsulated microgels and scaffolds have emerged as implantable or injectable biomaterials for the delivery of biological therapeutics, and numerous cell-tissue engineering applications.

By way of example, U.S. Pat. No. 7,226,617 to Ding et al. discloses a thermosensitive and biodegradable microgel and methods of making the same used for the controlled release of a drug or in tissue engineering and are suitable for the control release of biologically active substances such as proteins.

Further, U.S. Pat. No. 7,056,901 to Freceht et al. that discloses microgels, and microparticles made using a cross-linker molecule that contains a linkage cleavable under mild acidic conditions such as a bisacryloyl acetal crosslinker. These microgels and microparticles are meant to degrade in the lysosomal compartment within a cell and release their cargo into the cell.

Gel microencapsulation of cells is a promising strategy to support cell growth, modulate its behavior and alongside provide for immuno-isolation after transplantation. Microarrays of cell-encapsulated gels can be used to study cell behavior and survival, serve as building blocks to fabricate three dimensional tissues, cell delivery systems, and high throughput drug screening devices. Conventional design considerations for gel compositions included tunable mechanical and biochemical properties that could support growth of encapsulated cells. A rationally designed scaffold should allow for encapsulated cells to survive, adhere, proliferate, and remodel the niche, as well as deliver growth supporting molecules. Recently the paradigm has shifted towards developing bioengineered gels that recapitulate aspects of the cell-specific micro-environmental conditions in native tissues such as adhesive proteins and architecture. Current 3D tissue or cell culture platforms include multicellular spheroids grown in suspension, cells encapsulated within naturally derived ECM such as Matrigel and collagen, or non-degradable scaffolds fabricated using chemical, thermal or UV cross-linked methods.

For example, PCT/US2008/053287 application to Shea et al. discloses various compositions for making hydrogels that have improved mechanical properties for biological cultures and provides methods for making the hydrogels. Shea further discloses the hydrogels of the invention are useful for culturing follicles in vitro. The disclosed microgel are made from irradiated or oxidized alginate compositions.

Another example of a composition for use as a scaffold for encapsulated cells is disclosed in U.S. Pat. No. 7,449,180 to Kisiday et al., which discloses a scaffold of amphiphillic peptides to encapsulate a living cell. The scaffold for the encapsulated cells increase the mechanical stiffness of the scaffold such that the cells encapsulated therein can be used to replace endogenous cartilage tissue.

Polyethylene glycol (PEG) based gels consist of low-protein binding networks with proven minimal immunogenicity that have been widely used for in vivo testing. A vast majority of PEG-based gels are prepared using photo, thermal, or emulsion crosslinking approaches using microfluidics. In diacrylate functionalized PEG hydrogels, PEG macromers are cross-linked via free-radical reaction initiated by chemical activation or UV cleavage of a photoinitiator (e.g. Irgacure®).

Despite the advantages that many of these systems provide, many have serious drawbacks. For instance, photo-crosslinked hydrogels have been extensively studied over the past decade, yet a critical drawback of free-radical crosslinking is that it can significantly reduce the viability of encapsulated cells. Further, free-radical crosslinking is unwieldy for in situ delivery of cells and biomolecules through surgical needles. Although cell encapsulation in a microfluidic chip generated microgels using emulsification of hydrazide and aldehyde-functionalized carbohydrates without free radicals have been reported, bioactive adhesion molecules cannot be easily incorporated in such microgels, making the maintenance of cells requiring adhesive ligands for viability and function difficult.

Accordingly, there is a need in the art for engineered scaffolds that allow for encapsulated cells to survive, adhere, proliferate, remodel the niche, and deliver growth-supporting molecules. The present invention addresses this need.

The present invention and its attributes and advantages will be further understood and appreciated with reference to the detailed description below of presently contemplated embodiments, taken in conjunction with the accompanying drawings.

SUMMARY OF THE INVENTION

The present disclosure provides for a bio-adhesive gel composition with favorable modular dimensions, mechanical properties and bulk modified biomolecule compositions fabricated using, in some embodiments, a Michael-type addition chemistry to crosslink a gel composition, creating an interpenetrating network useful in growing and studying various cell types in a microenvironment similar to the cell's natural environment. Further, the compositions described herein are also useful as a model system for testing the efficacy of various bioactive and chemotherapeutic agents on different cell types such as cancers, including hematological cancers such as lymphomas.

The present disclosure is directed to gel compositions comprising a polymerized maleimide-functionalized poly alkylene oxide, an adhesive protein, and a nanoparticle where the adhesive protein and nanoparticle form an interpenetrating network through the maleimide-functionalized poly alkylene oxide. In other embodiments, the adhesive protein comprises proteins or peptides. In other embodiments, the adhesion protein comprises a gelatin or collagen. In other embodiments, the nanoparticle comprises a silicate nanoparticle and the maleimide-functionalized poly alkylene oxide comprises a maleimide-functionalized polyethylene glycol.

In other embodiments, the gel composition can contain a thiol-containing compound that readily undergoes a Michael-type addition reaction to fabricate the gel composition. The Michael-type addition reaction is desirable because it allows crosslinking of substrates at physiological pH and temperature, while only requiring a nucleophilic buffer. This process eliminates the need for a harsh chemical crosslinker or damaging UV radiation that may adversely affect an encapsulated cell.

In specific embodiments, the gel composition with an interpenetrating network comprises a maleimide-functionalized poly alkylene oxide of about 0.1%-10% w/v, an adhesive protein of about 0.1%-7.5% w/v, a silicate nanoparticle of about 0.1%-2% w/v, and a thiol-containing compound. In other specific embodiments, the gel composition comprises about 2.5% w/v of maleimide-functionalized polyethylene glycol, about 0.5% w/v of gelatin, about 0.3% w/v of silicate nanoparticles and a thiol-containing compound In some embodiments, the thiol-containing compound is dithiothreitol or a cysteine residue.

The interpenetrating networks of the gel composition functions to provide structurally stable and a suitably porous microenvironment. Accordingly, such a gel composition is desirable for encapsulating cells. For example, the encapsulated cell can be a normal cell or a cancer cell. In some embodiments, the cancer cell is a hematological cancer cell. In further embodiments, the hematological cell is a lymphoma, leukemia or myeloma. In some instances, the compositions can comprise a chemotherapeutic agent.

In other aspects of the disclosure, there is provided a gel cell culture system that provides a three dimensional microenvironment for an encapsulated cell. Such a system comprises a maleimide-functionalized poly alkylene oxide of about 0.1%-10% w/v, an adhesion protein of about 0.1%-7.5% w/v, a nanoparticle of about 0.1%-2% w/v, and a thiol-containing compound where the maleimide-functionalized poly alkylene oxide and the thiol-containing compound form a first network, and the adhesion protein and the nanoparticle form a second network where the second network interpenetrates through the first network.

Such a system can further comprise various types of cells such as, but not limited to a normal cell, benign cell, cancer cell, immortalized cell, genetically engineered cell, stem cell or patient derived primary cell. Moreover, cancer cells, for instance can comprise a hematological cancer cell such as a lymphoma or a myeloma or a leukemia. The lymphoma can comprise a T-cell Non-Hodgkin Lymphoma and a B-cell Non-Hodgkin Lymphoma or a combination thereof.

The system described herein can have superior biomedical and pharmacological research attributes due to the nature of the gel composition. For instance, because the gel composition is very tunable in various physical characteristics, the system can be adjusted for optimal growth conditions for a desired cell type, or for studying various cellular processes, or studying the effects of various bioactive or chemotherapeutic agents, as well as other drugs/agents. For instance, the system can be used to study the following cellular effects on a cell encapsulated within the 3-dimensional-gel microenvironment including, but not limited to cell growth, proliferation, differentiation or de-differentiation, inhibition of cell growth proliferation, cell death, cell survival, necrosis or inhibition of necrosis, cell-cell interaction, release of a cellular factor, transmitter or agent, release or uptake of an ion, change in cell adhesion, morphology or migration, or a change in an intracellular or extracellular signaling pathway. These characteristics can be observed prior to, during and after administration of a bioactive or chemotherapeutic agent.

In some embodiments, the gel composition, systems and methods can comprise a hydrogel, a microgel, arrays or microarrays.

In further embodiments, the gel compositions can be fabricated to contain multiple layers of interpenetrating networks. The layers can be identical or non-identical layers. In other embodiments, the layers form separate layers of interpenetrating networks. In still further embodiment, the layers are non-separable. In other embodiments, the multiple layers of interpenetrating networks can be manipulated to mimic different tissue types by incorporation of various cell types, proteins and other biological components In further embodiments, the present disclosure is directed to a method of testing the efficacy of a chemotherapeutic agent in treating a cancer cell that comprises contacting a composition of the present disclosure (such as a composition comprising an interpenetrating network of gelatin, a silicate nanoparticle, a maleimide-functionalized polyethylene glycol and a thiol-containing compound such as dithiothreitol) with a chemotherapeutic agent and observing a cellular effect of the chemotherapeutic agent on a cell or on a microenvironment of the cell.

The method further comprises the steps of acquiring a first measurement of the cellular effect on the cancer cell prior to contacting the composition having the chemotherapeutic agent and comparing the first measurement of the cellular effect on the cancer cell to a second measurement of the cellular effect after contacting the composition having the chemotherapeutic agent. The method can measure various cellular effects such as cell growth, proliferation, inhibition of cell growth proliferation, differentiation or de-differentiation, cell death, cell survival, necrosis or inhibition of necrosis, cell-cell interaction, release of a cellular factor, transmitter or agent, release or uptake of an ion, change in cell adhesion, morphology or migration, or a change in an intracellular or extracellular signaling pathway. The method can measure any number of the above listed effects.

In some embodiments of the method, the cancer cell comprises a hematological cancer cell.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF EMBODIMENTS OF THE INVENTION

Figure 1:
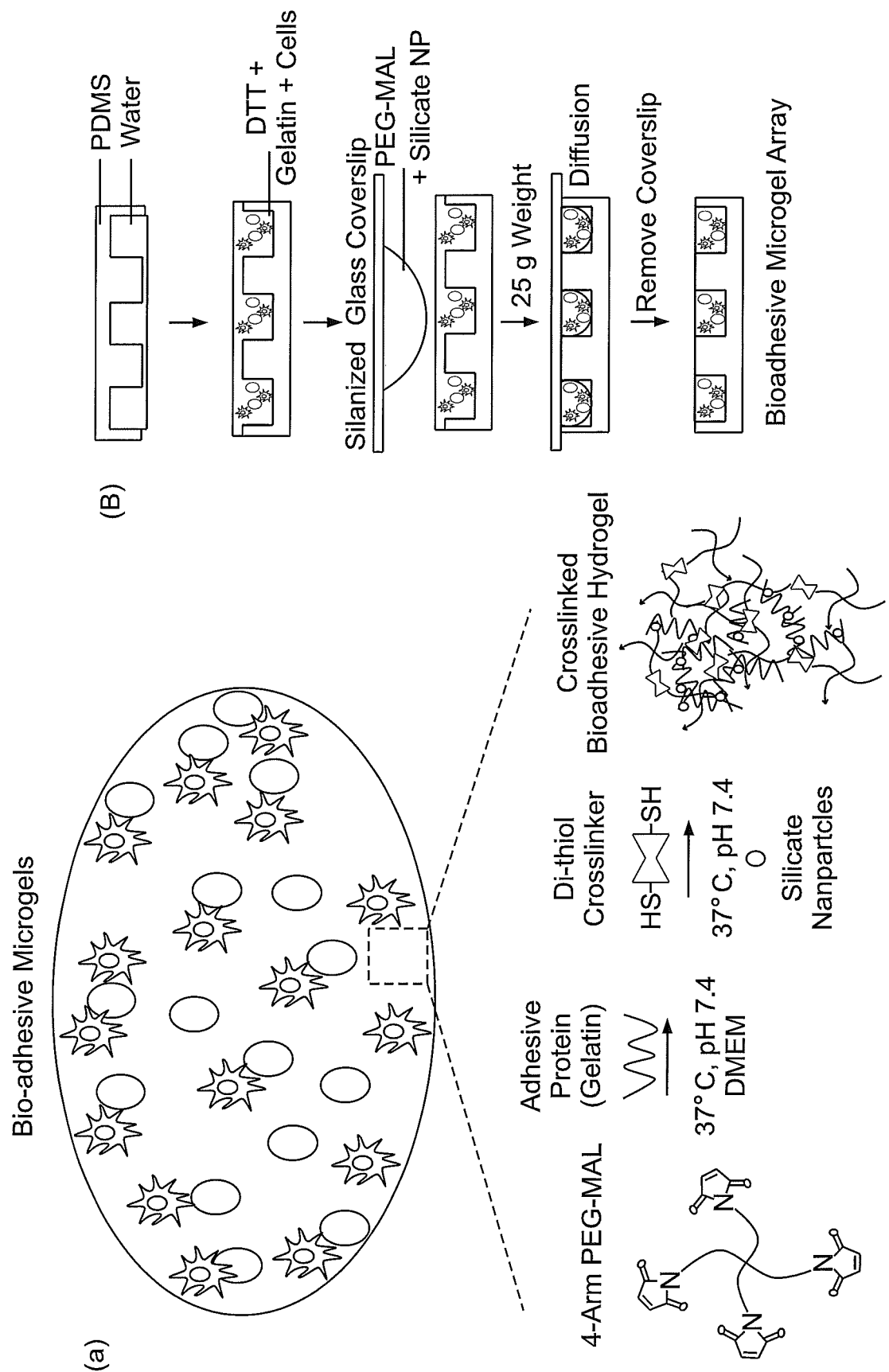
FIG. 1 illustrates a bio-adhesive, cell encapsulated interpenetrating networks of PEG-MAL and gelatin-silicate nanoparticles (NP). (1a) A schematic of bio-adhesive cell supportive microenvironment consisting of 4-arm PEG-MAL cross-linked with DTT and coated with a stable interpenetrating network of gelatin with silicate NP. The 4-Arm PEG-MAL undergoes a Michael-type addition reaction with thiol groups on DTT and gelatin forms an ionic gelation complex with NPs at 37° C. and pH 7.4. The PEG component provides structural support for cells while the gelatin-NP component provides adhesive ligands for cell spreading and signaling. The spheres represent suspension cells and star-shaped cells are anchorage-dependent. (1b) A schematic representing microfabrication of bio-adhesive microgels. Component B consisting of 4-arm PEG-MAL precursors were mixed with silicate NPs and media with or without cells and poured onto a PDMS microwell mold. Component A consisting of a well-mixed solution of gelatin with DTT and media was placed on a Sigmacote-coated glass slide and aligned with Component B on each micromold, allowing the polymers to diffuse and mix. After 1 minute, glass slides were removed leaving behind an array of cell encapsulated microgels.

The present disclosure provides a gel composition with novel characteristics that allow the gel compositions to be tuned to the user's requirements. Gel compositions of the present disclosure are tunable for mechanical and biochemical properties to support cell growth. Some of the advantages that these characteristics provide, include but are not limited to tunable swelling and reaction rates, facile and stoichiometric incorporation of adhesive ligands, increased stability, negligible cell-mediated swelling, enhanced cell spreading and improved metabolic activity and degradation properties.

Furthermore, the use of Michael-type addition chemistry to crosslink the gel composition eliminates the use of harsh chemical and UV crosslinking components. These and other advantages will be described in further detail below.

Embodiments of the present disclosure include gel compositions that form an interpenetrating network wherein a first network generally comprises a functionalized poly alkylene oxide and a linking agent and a second network that comprises an adhesive protein and a nanoparticle. The second network interpenetrates the first network. Such compositions, which mimic a cell's natural environment, can be used for a variety of applications that comprise gels (e.g. hydrogels, microgels), three dimensional microenvironments for supporting, growing and examining encapsulated cells, as well as to provide model systems for drug testing, such as testing chemotherapeutic or other agents on diseased cells (e.g. cancer cells).

The gel compositions described herein comprise at least one functionalized poly alkylene oxide. The term "poly alkylene oxide" as used herein refers to a class of compounds comprising at least two repeating units comprising an ether-alkyl group wherein the alkyl group forming the backbone of the repeating unit comprises from 2 to 3 carbon atoms which may be un-substituted or substituted. Non-limiting examples of applicable substituent groups include: hydroxyl, carboxylic acid, alkyl, and alkoxy wherein alkyl and alkoxy groups may be un-substituted or substituted with substituent groups such as hydroxyl and epoxy.

The poly alkylene oxide compound may be linear, branched, comb, brush, star or dendritic, or include combinations of such compounds. Specific examples of compounds include: polyethylene glycol, polyethylene glycol monoalkyl ethers, trimethylolpropane ethoxylate, pentaerythritol ethoxylate, and glycerol ethoxylate, polyethylene glycol monoglycidyl ether, poly(ethylene glycol) 2-aminoethyl methyl ether, polyethylene glycol mono (2-aminoethyl)ether, polyethylene glycol diamine, polyethylene glycol bis(3-aminopropyl)ether, polyethylene glycol diglycidyl ether; polyethylene glycol bis(2-chloroethyl) ether, polyethylene glycol bis(2-bromoethyl)ether, polyethylene glycol 2-chloroethyl methyl ether, polyethylene glycol 2-bromoethyl methyl ether, sulfonate of polyethylene glycol methyl ether and $\alpha,\omega$-disulfonate of polyethylene glycol, or any combination thereof. In some embodiments, the poly alkylene oxide is polyethylene glycol.

The poly alkylene oxide compounds are preferably water soluble, i.e. soluble at concentrations of at least about 0.1 wt %, preferably at least about 1 wt %, and even more preferably at least about 10 wt % at 25° C. and 101 kPa (1 atm).

According to the present disclosure, the poly alkylene oxide is functionalized to be reactive with thiol-containing compounds.

In some embodiments, the poly alkylene oxide is functionalized with a maleimide or maleimide containing functional group. As used herein, a maleimide is a cyclic unsaturated imide of the formula $H_2C_2(CO)_2NH$, which is reactive with the free sulfhydryls in cysteine residues or other thiol-containing compounds and can also react with free amines in lysine and histidine residues to a lesser extent.

In some embodiments, the maleimide functionalized poly alkylene oxide is a maleimide functionalized polyethylene glycol.

Generally, the maleimide is situated at each end of the poly alkylene oxide molecule, and can further include multiple maleimides. In some embodiments, the poly alkylene oxide (e.g. polyethylene glycol) can contain at least 2, at least 4, at least 6 or at least 8 maleimides. In some embodiments, the maleimide functionalized poly alkylene oxide is a 4-branched maleimide functionalized polyethylene glycol.

Embodiments of the present disclosure further comprise an adhesive protein. The term adhesive protein is used herein to refer to polymers, proteins, small peptides or amino acids such as those found in or derived from biological systems. For example, adhesive proteins for use in the present disclosure include but are not limited to gelatin, collagen, elastin, fibronectin, fibrin, vitronectin, laminin-1 to 12, tenascin, thrombospondin, von Willebrand factor, osteopontin, pectins, albumin, ovalbumin, cadherins, desmocolin, desmoglein, integrins, E-selectin, P-selectin, L-selectin, polyamino acids (e.g. polylysine), RGD peptides or proteins, whey protein, glycoproteins or combinations thereof. In some embodiments, the adhesive protein comprises gelatin and/or collagen, and or small peptides, or a combination thereof. In certain embodiments, the adhesive protein comprises a gelatin.

Embodiments of the present disclosure further comprise a nanoparticle. The term "nanoparticle", as used herein is a general term that encompasses particulate material having a dimension between about 1 nm to about 400 nm, preferably between 1 nm and 300 nm, and more preferably between 2 nm and 200 nm and most preferably from 1 nm to 100 nm. The shapes of the nanoparticles are not particularly critical: spherical nanoparticles particles are typical. Where non-spherical nanoparticles are employed, "diameter" is meant to refer to the diameter of a hypothetical sphere having the same volume of the non-spherical nanoparticle. For the purposes of the present disclosure, "a substantial portion" of the nanoparticles are to be deemed to have a specified diameter or a specified range of diameters when more than 50% (e.g., more than 60%, more than 65%, more than 70%, more than 75%, more than 80%, more than 85%, more than 90%, etc.) have diameters of the specified diameter or within the specified range of diameters.

In some embodiments, the diameter of the nanoparticle is about 10 nm-40 nm, or more preferably about 20 nm-30 nm in diameter.

Nanoparticles of the present disclosure can comprise, for example, silicate, zinc oxide, silicon dioxide, metals, metal oxides, polymers, fullerenes or composites thereof. In some embodiments, the nanoparticles are synthetic silicate nanoparticles. In further embodiments, the nanoparticles are synthetic silicate nanoparticles having a diameter of about 20 nm-30 nm. In still further embodiments, the synthetic silicate nanoparticles have a thickness of about 1 nm.

The linking agent used herein is preferably a thiol-containing compound that can be cross-linked to the functionalized poly alkylene oxide. The thiol-containing compound can be a bi-functional or branched thiolated compound. Preferably, the thiol-containing compound is, for example a cysteine amino acid, or a peptide or proteins containing at least one cysteine amino acid, or dithiothreitol. In specific embodiments, the linking agent is dithiothreitol. In some instances, the cross-liking agent is a reversible cross-linker. In other instances, the cross-linking agent is non-reversible. In still further instances, the cross-linking agent is degradable by chemical agents, environmental conditions, proteases or other biological components It is preferable that the cross-linking of the functionalized poly alkylene oxide and the linking agent occur through a Michael-type addition reaction. A Michael-type addition is desirable because the free thiol groups of the thiol-containing compounds readily react with suitable moieties such as maleimides, vinyl sulfones, acrylates, acrylamides, acrylonitriles and methacrylates. Furthermore, the Michael-type addition reaction readily occurs at a physiological pH and only requires a nucleophilic buffer (e.g. triethanolamine, HEPES, Dulbecco's Modified Eagles Medium (DMEM)), however, some of these buffers, such as triethanolamine maybe unsuited for the embodiments disclosed herein because triethanolamine could have cytotoxic effects on sensitive cell types such as endothelial cells. The Michael-type addition provides a covalent cross-linking reaction without the need for harsh chemical cross-linkers that can produce free-radical species or UV cross-linking, either of which can inhibit cell growth or other cellular characteristics, or be lethal to a cell encapsulated therein.

In some embodiments, the gel composition comprises a maleimide-functionalized poly alkylene oxide covalently cross-linked to dithiothreitol using a Michael-type addition reaction. In other embodiments, the gel composition comprises a maleimide-functionalized polyethylene glycol, or other branched maleimide functionalized polyethylene glycols covalently cross-linked to dithiothreitol using a Michael-type addition reaction. The dithiothreitol concentration is preferably less than 70 mM, and more preferably less than 4.5 mM.

In other embodiments, the gel composition comprises a polymerized maleimide-functionalized polyethylene glycol, an adhesive protein, and a nanoparticle wherein the adhesive protein and the nanoparticle form an interpenetrating network through the maleimide-functionalized polyethylene glycol.

In further embodiments, the adhesive protein can be a protein or a peptide. In further embodiments, the adhesive protein can be a gelatin or collagen. In other embodiments, the nanoparticle is preferably a silicate or synthetic silicate nanoparticle. In still further embodiments, the adhesion protein may include a plurality of adhesion proteins. These embodiments are preferably fabricated using a thiol-containing compound Michael-type addition chemistry.

Generally, the first network comprising the functionalized maleimide poly alkylene oxide (e.g. polyethylene glycol) is covalently cross-linked to a thiol-containing compound (e.g. dithiothreitol). The second network comprising an adhesive protein (e.g. a protein, peptide, gelatin or collagen) and nanoparticles (e.g. silicate) are ionically cross-linked and form an interpenetrating network where the second network interpenetrates the first network. This interpenetration of the two networks forms a substantially homogenous polymerized gel composition. However, in some embodiments, the gel composition may be heterogeneous. The two interpenetrating networks are generally inseparable from one another. The interpenetration of the two networks also forms a favorable microenvironment for the growth and study of various types of biological cells including any cells naturally found in the body, as well as those cell that have been genetically modified. Further, the cells can be cancerous cells. The growth, manipulation, testing and examination of the various cell types will be described in more detail below, and in the Examples.

By varying the amounts of specific components of the gel composition, it is possible to manipulate the gel composition properties as needed by the user. For example, these include such properties as hydrolytic swelling and degradation, metalloproteinase-mediated degradability, contraction, cell spreading and co-encapsulation of anchorage dependent and anchorage independent cell types.

Figure 3:
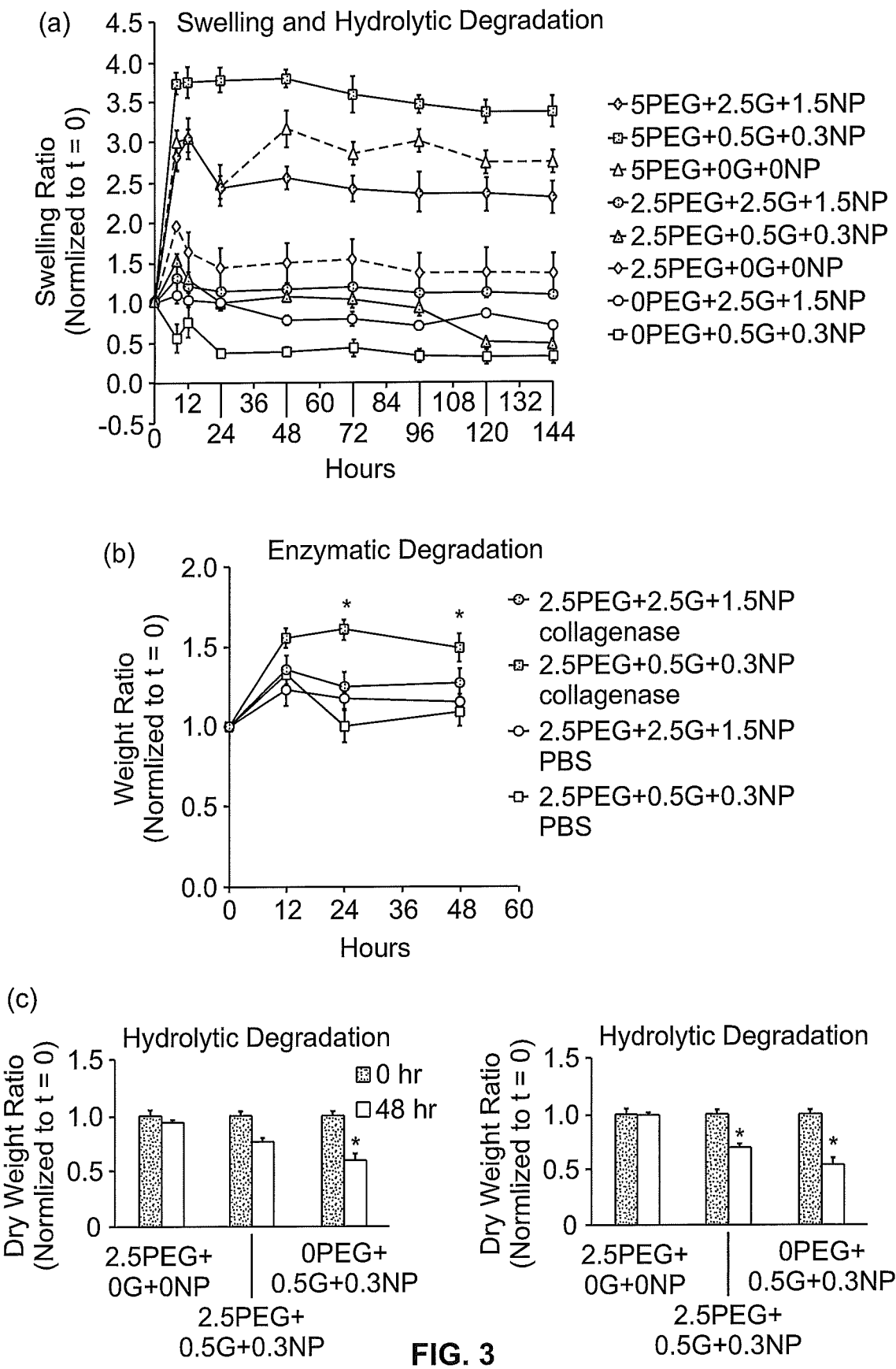
FIG. 3 illustrates hydrogel swelling and degradation profiles. (3a) The swelling and degradation profiles of various crosslinking network formulations under hydrolytic conditions, (3b) Degradation profile when enzymatically treated with collagenase. (*p<0.05 with respect to gels not exposed to collagenase, n=3). (3c) Ratio between dry weight at 0 and 48 h for various compositions under hydrolytic and enzymatic conditions (n=3).

The Applicants have found that by manipulating the amounts of adhesive protein, functionalized poly alkylene oxide and nanoparticles that form the interpenetrating networks can greatly affect the swelling ratios of the gel compositions. In a specific example, the incorporation of greater than 2.5% maleimide-functionalized polyethylene glycol showed greater swelling compared to that of gel compositions having 2.5% or less maleimide-functionalized polyethylene glycol. Moreover, gels having maleimide-functionalized polyethylene glycol showed minimal hydrolytic degradation as compared to gel compositions without maleimide-functionalized polyethylene glycol (FIG. 3).

Furthermore, the Applicants investigated the matrix metalloproteinase-mediated degradability of the gel composition. This is an important facet of such compositions because it relates to niche remodeling, cell spreading, and intra-gel migration of cells. A certain degree of metalloproteinase degradation is desirable, yet too much degradation can lead to destruction of the microenvironment and eventually cell death. As shown in FIG. 3, gel compositions with 2.5% polyethylene glycol, 0.5% gelatin and 0.3% silicate nanoparticles showed a two-fold increase in gel wet weight over the same gel compositions not treated with a collagenase for the same time period. Gel compositions with 2.5% polyethylene glycol, but having a higher percentage of gelatin and nanoparticles showed a lower increase in gel wet weight indicative of a lower degree of enzymatic degradation. In contrast, gel compositions comprising only gelatin will not form a gel in the presence of a metalloproteinase.

Lastly, a technical problem encountered with some gel compositions is the phenomenon of cell-mediated contraction of the surrounding microenvironment that has a negative effect on long-term growth of a cell therein.

The Applicants found that incorporation of at least 2.5% maleimide-functionalized polyethylene glycol, at least 0.5% gelatin and at least 0.3% silicate nanoparticles showed no cell-mediated contraction when these gel compositions contained mouse fibroblast cells.

In a specific embodiment that takes advantage of the aforementioned characteristics, the gel composition comprises about 0.1%-10% w/v of maleimide-functionalized polyethylene glycol, about 0.1%-7.5% w/v gelatin and about 0.1%-2% w/v of synthetic silicate nanoparticles and dithiothreitol.

In a further specific embodiment, the gel composition comprises about 2.5% w/v of maleimide-functionalized polyethylene glycol, about 0.5% w/v of gelatin and about 0.3% w/v of synthetic silicate nanoparticles and dithiothreitol. These embodiments are preferably fabricated using the previously described Michael-type addition reaction.

The gel composition disclosed herein can further comprise hydrogels and microgels and can be fabricated in various ways. These gels can also be formed into arrays and microarrays as desired.

As used herein, the term "hydrogel" describes a fibrous three dimensional network formed of water-soluble natural or synthetic polymer chains, typically containing more than 80% of an aqueous medium (e.g., water or an aqueous solution) and 20% or less of the polymeric material. Hydrogel refers to particles of gel of any shape, formed of cross-linked polymeric networks, having an average diameter greater than 1000 μm.

The term "microgel" as used herein refers to particles of gel of any shape, formed of cross-linked polymeric networks, having an average diameter of approximately 100 to 500 μm, such as about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1000 μm.

In some embodiments, as shown in FIG. 1, a mold is first fabricated. The mold preferably is made of polymethylsiloxane (PDMS). Alternatively, polymeric substrate materials may be used to fabricate the devices of the mold, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), thermoplastic elastomers and the like.

The PDMS molds are preferably pre-treated in plasma cleaner to make the micro wells hydrophilic. Preferably, the precursors to the microgel were mixed to form two separate component mixtures, the first mixture comprising the adhesive protein, linking agent and nucleophilic buffer (for example, gelatin, dithiothreitol and DMEM respectively). The second mixture comprising of maleimide functionalized poly alkylene oxide, nanoparticle and a nucleophilic buffer (for example, maleimide functionalized polyethylene glycol, a synthetic silicate nanoparticle and DMEM, respectively).

In some embodiments, if a biological cell is desired to be encapsulated within the microgel composition, the cells can be added to the first mixture.

Next, a droplet of the first mixture is placed on the mold, while a droplet of the second mixture is placed on a siliconized glass slide and placed on top of the mold and allowed to diffuse through the layer of the first component. Weight can be placed on the top of the slide to remove any excess solution. After one minute, the slide was removed and the resulting mixture placed in growth media to cure for 1 hour, preferably at about a pH of 7.4. In some embodiments, the above formed gel compositions are fabricated into microarrays on suitable substrates such as glass slides or other types of substrates known in the art. Microarrays are typically small, high throughput chips generally made of a solid support structure, typically glass slides, nitrocellulose, or microtiter plates.

Generally, the microarrays may contain any number of wells filled with a gel composition of the present disclosure including, but not limited to 10, 20, 30, 40, 50, 60, 70, 80, 90, 100, 200, 300, 400, 500 or more. The number of wells can be manipulated during fabrication of the well molds.

In other embodiments, the two mixtures were mixed without a mold to create a bulk gel (hydrogel).

Figure 9:
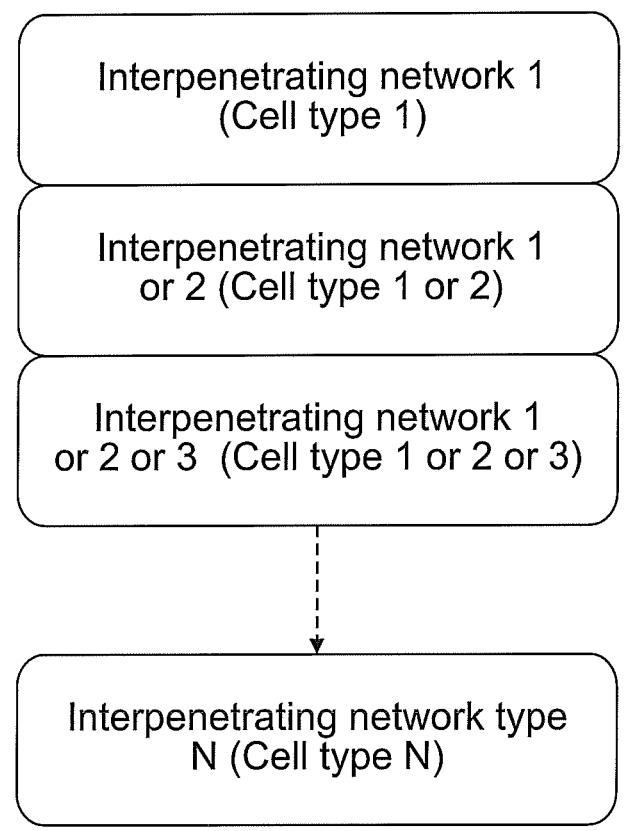
FIG. 9 illustrates layers of interpenetrating networks. The layers can be fabricated as a sandwiched layer of hydrogels or microgels for patterned tissue where each layer can comprise a different interpenetrating network and contain cells of any type and origin.

In further embodiments, the gel compositions can also be formed into multiple layers of interpenetrating networks. These layers can be poured on top of each other prior to complete solidification of any individual layer beneath it. This allows the user to design integrated patterned tissue layers. Alternatively, gelled layers can simply be placed on top of each other and removed as necessary (FIG. 9).

In some embodiments, the gel compositions can comprise at least 2, 3, 4, 5, 6, 7, 8, 9, 10 or more layers of interpenetrating networks. The layers can be the same or different from each other. By way of example, each layer can differ in the type of adhesion protein, maleimide-functionalized poly alkylene oxide, thiol-containing compound, nanoparticle, size of nanoparticle, cell type encapsulated therein, chemotherapeutic or bioactive agent, a combination thereof, or another molecule added to the different layers.

The layers can be designed to differ in properties such as, but not limited to stiffness, degradability, cellular growth of encapsulated cells, diffusion properties, cell spreading, porosity and other features as described herein. Further, these layered gels can be manipulated to support the growth of specific cell types in a particular layer.

In some embodiments, the layers are separate from one another. In other embodiments, some of the layers are separate from one another. In still further embodiments, the layers can be removed or peeled off from the other layers using manual, chemical, thermal, or enzymatic removal techniques.

The gel compositions with interpenetrating networks according to the present disclosure may be useful as scaffolds to support, grow and study living cells and their microenvironment. The gel composition can support living cells within the 3-dimensional microenvironment formed by the interpenetrating networks, allowing the cells to grow, spread or otherwise proliferate. These cells are preferably encapsulated within the gel composition.

The living cells may also be in a diseased state, such as cancer cells. Thus, in some embodiments, the present disclosure provides a gel composition in which or on which diseased living cells are supported and can serve as a tool for the study of the biology of diseased cells. The gel composition may include any of the gel substituents described herein. In some embodiments, the gel composition for studying various cells may comprise about 0.1%-10% w/v of maleimide-functionalized poly alkylene oxide, about 0.1%-7.5% w/v adhesion protein and about 0.1%-2% w/v of synthetic silicate nanoparticles and a thiol-containing compound.

In other embodiments, the gel composition for studying various cells may comprise about 0.1%-10% w/v of maleimide-functionalized polyethylene glycol, about 0.1%-7.5% w/v gelatin and about 0.1%-2% w/v of synthetic silicate nanoparticles and dithiothreitol.

In still further embodiments, the gel composition comprises about 2.5% w/v of maleimide-functionalized polyethylene glycol, about 0.5% w/v of gelatin and about 0.3% w/v of synthetic silicate nanoparticles and dithiothreitol.

In some embodiments, the gel composition can be useful to culture an encapsulated cell wherein the mechanical properties of the gel composition can be tuned to facilitate optimal cell growth, cell spreading and niche remodeling.

Figure 5:
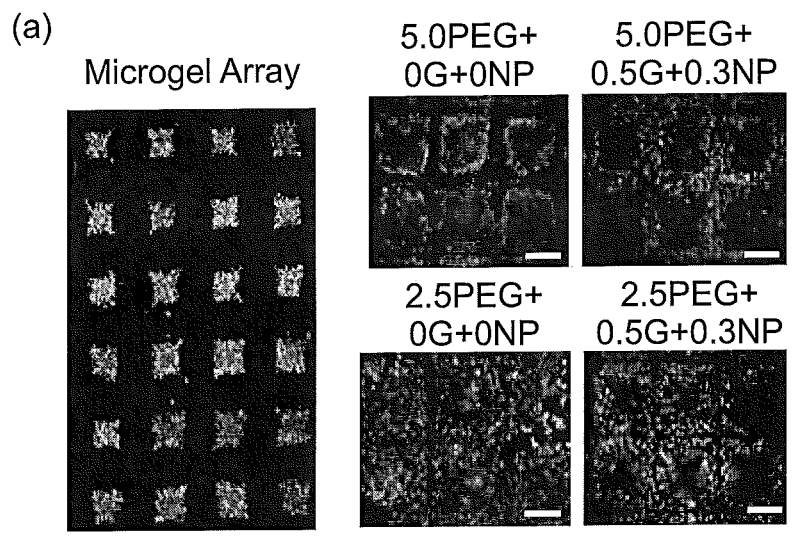
FIG. 5 illustrates Live/Dead cytotoxicity studies of encapsulated cells. (5a) Fluorescent micrograph of a representative microgel array at t=0. Individual panels for each microgel group represents live and dead cells on day 3. Scale Bar=200 μm. (5b) Scatter plot of cell viability profiles for each microgel formulation over a period of 72 h. All samples were seeded with 4×10$^5$ cells at t=0. Data represents % survival normalized to t=0. * p<0.05 compared to all other groups at 72h; $p<0.05 compared to 5% PEG-MAL only gels (diamond) at 72 h. n=16. (5c) 3D reconstruction of a whole 2.5 P+0.5 G+0.3 NP microgel with individual z-sections at indicated depth.
Figure 5:
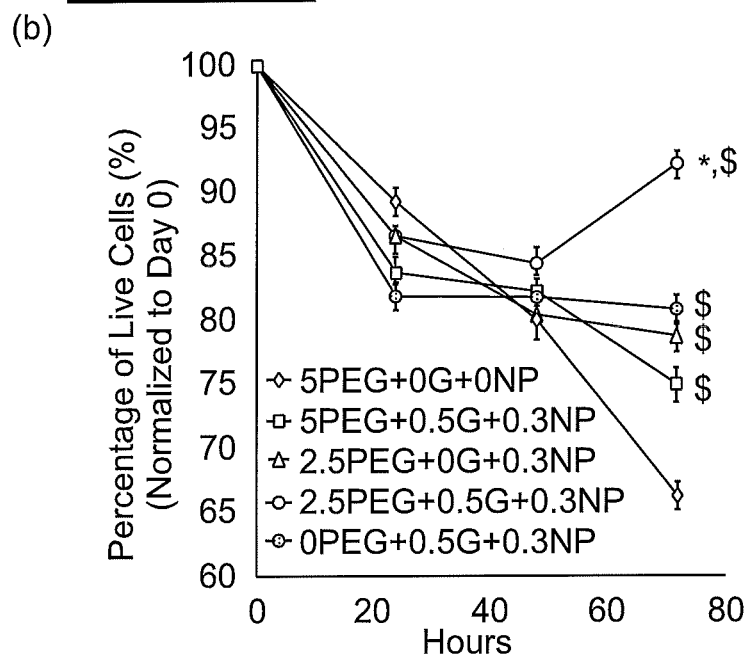
Figure 5:
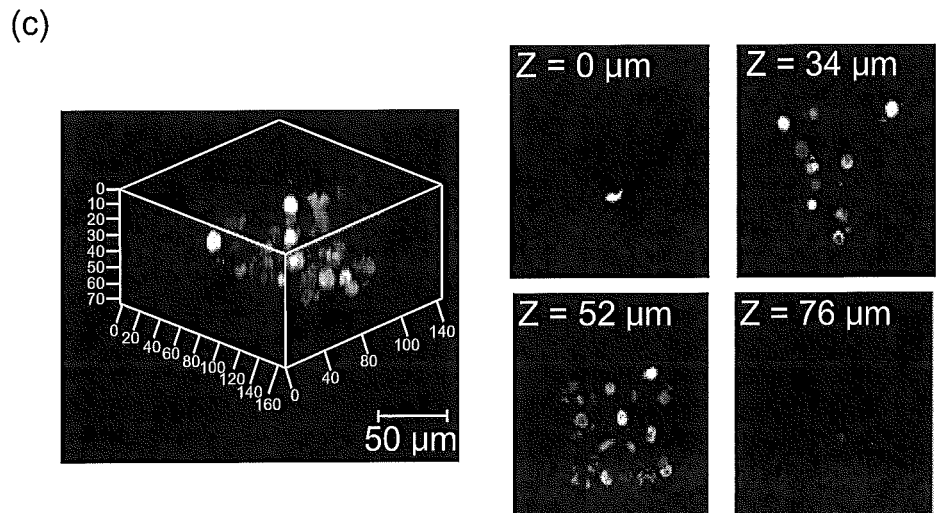
Figure 7:
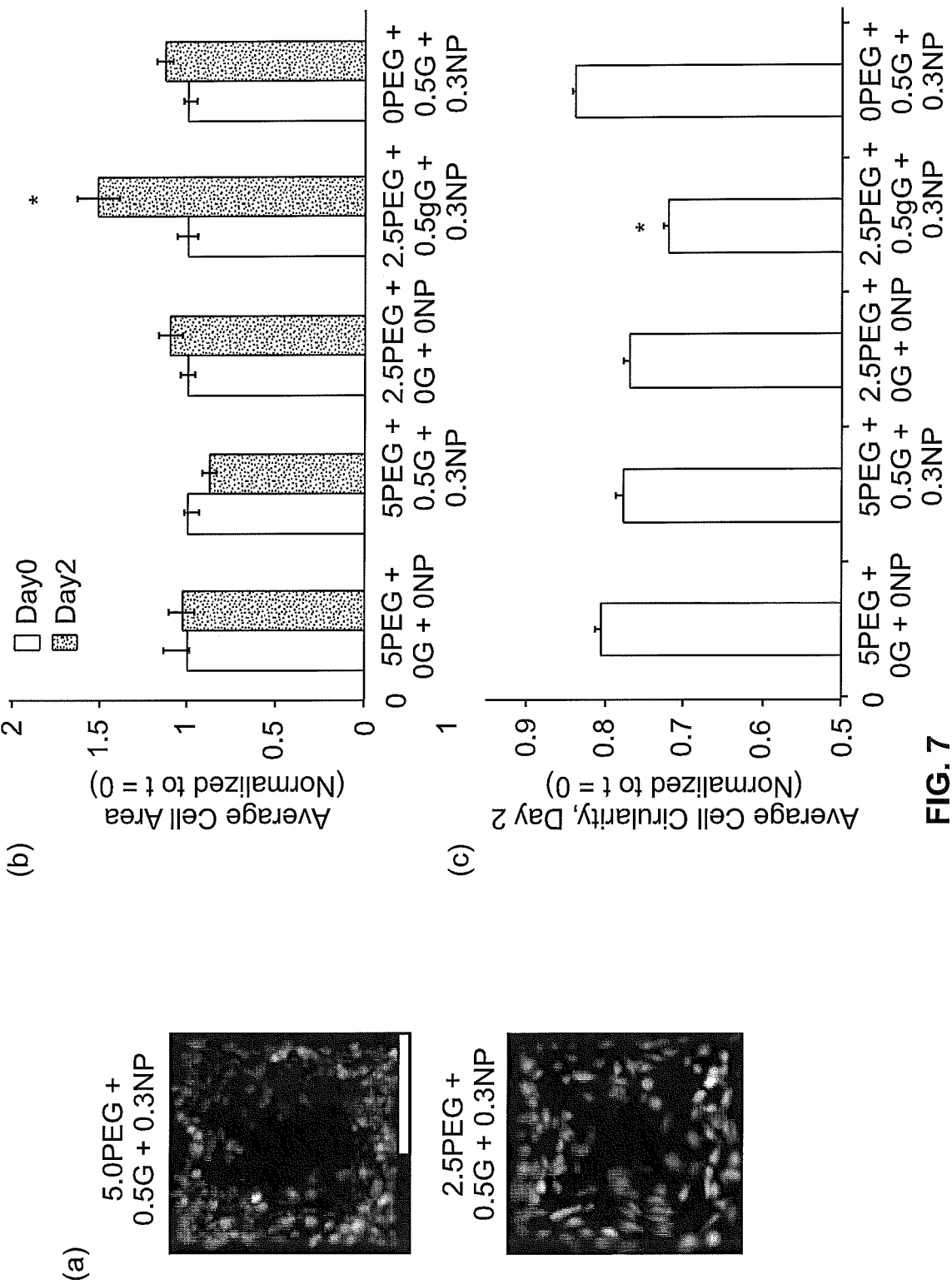
FIG. 7 illustrates anchorage-dependent cell spreading. (7a) Fluorescence micrographs represent spreading behavior of encapsulated HeLa cells in representative microgel formulations. (7b) Bar graph represents average cell spreading for each microgel group, normalized to day 0 spreading areas. *p<0.05 compared to all microgel groups on day 2. n=5. (7c) Bar graph represents average cell circularity indicative of change in cells shape and spreading. *p<0.05 between compared all other microgel groups. n=6.

For example, the Applicants have found that gel compositions as described herein demonstrate excellent cell survivability. Gel compositions with gelatin, maleimide-functionalized polyethylene glycol and silicate nanoparticles showed superior cell viability compared to gels without gelatin or silicate nanoparticles after a 72 hour period. Surprisingly, cell viability increased after 72 hours for gel compositions containing 2.5% maleimide-functionalized polyethylene glycol, 0.5% gelatin and 0.3% silicate nanoparticles, indicative of cell proliferation and spreading (FIGS. 5, 7).

Figure 8:
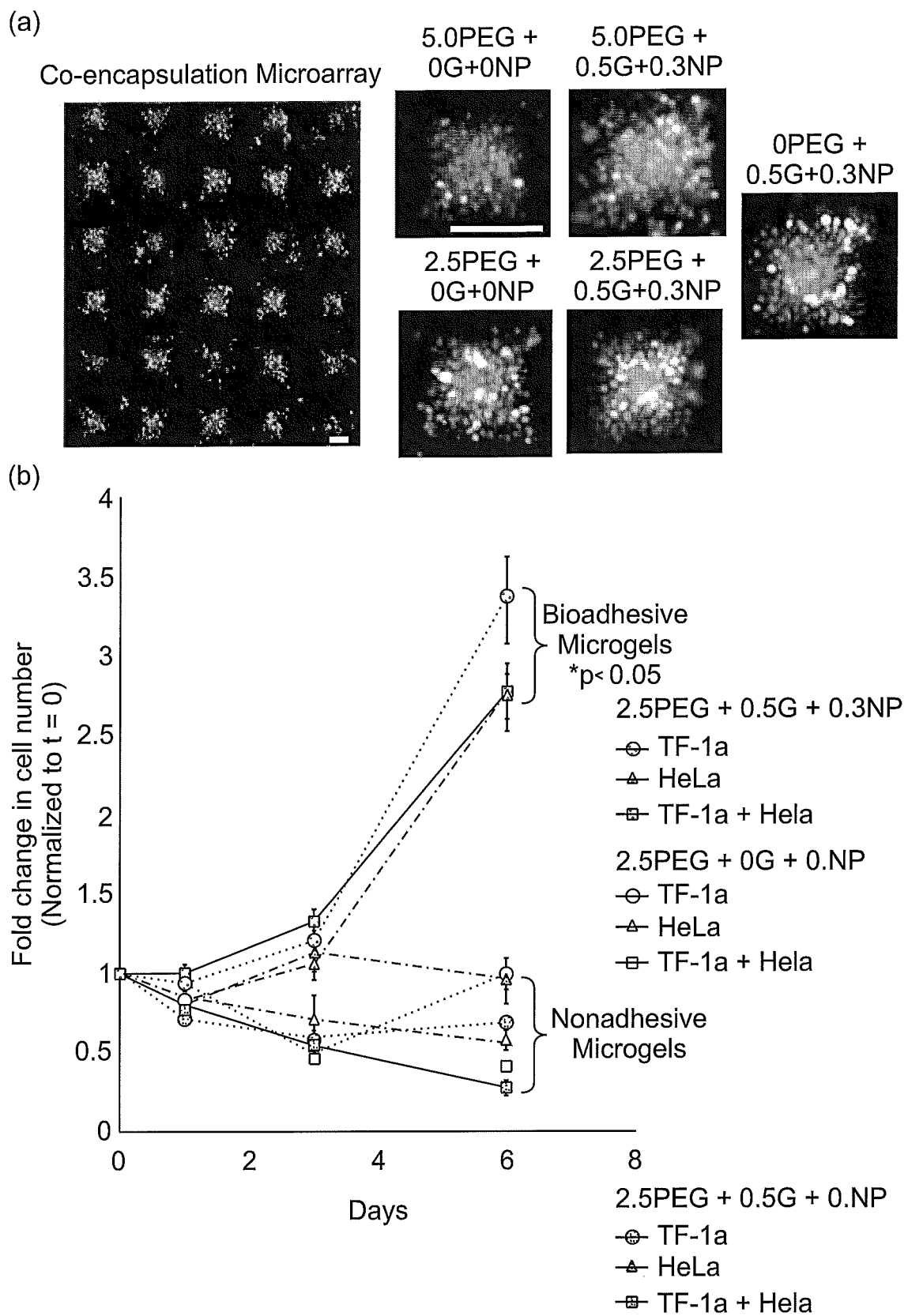
FIG. 8 illustrates suspension cell co-encapsulation and long term metabolic activity. (8a) A suspension of 2×10$^5$ TF-1a leukemia and 1×10$^5$ adhesive HeLa cells, pre-stained with Cell Tracker™ dye, were co-encapsulated inside each microgel. Scale Bar=200 μm. (8b) In vitro cell proliferation (metabolic activity) was assessed in microgels using Cell-Titer 96® AQueous One Solution Cell Proliferation assay solution. *p<0.05 compared to nonadhesive microgel groups. n=3.

Another advantage to gel compositions described in the present disclosure is the ability to encapsulate multiple types of cells into the gel microenvironment. While helpful in many ways, the ability to successfully incorporate multiple cell types is particularly important, for instance, in studying both anchorage dependent and anchorage independent cells. Gel compositions having 2.5% maleimide-functionalized polyethylene glycol, 0.5% gelatin, and 0.3% silicate nanoparticles showed excellent cell viability of anchorage dependent and anchorage independent cells and metabolic activity when compared to other gel compositions (FIG. 8).

Further, the Applicants have found that the gel compositions as described herein have the desirable characteristic of being in a solid state when heated up to a temperature of 37 degrees Celsius. This is desirable because this is an optimum temperature for cell growth and helps to further mimic the natural environment of the cell.

The cells used herein are preferably human cells, but can also be other Eukaryotic cells such those cells derived from an animal such as, but not limited to primates, rodents, felines, canines, poultry, ruminants, equine and swine. The cells can also be obtained from a biological sample taken from a subject, human or otherwise, having or suspected of having cells in a diseased state. In some instances, the disease state may be cancer.

As used herein, "obtained from a biological sample" or "obtaining a biological sample" refers to such methods as will be well known to the skilled worker. A biological sample may be obtained directly or indirectly from the subject. The term "obtaining" a biological sample may comprise receiving a biological sample from an agent acting on behalf of the subject. For example, receiving a biological sample from a doctor, nurse, hospital, medical center, etc., either directly or indirectly, e.g. via a courier or postal service.

In other examples, a sample containing cells, diseased cells, cancerous cells or suspected as containing diseased cells is obtained from the subject using a fine needle aspirate (FNA) sample. Methods of obtaining a FNA sample, processing and/or storage of such a sample are also well known to the skilled worker. In other examples, a sample is obtained from surgical dissection. In other embodiments, a physician prepares the samples or other qualified individual and provided for examination.

The term "sample" as used herein, encompasses a variety of cells, cell-containing bodily fluids and/or secretions as well as tissues including, but not limited to a cell(s), tissue, whole blood, blood-derived cells, plasma, serum, tumors, sputum, mucous, bodily discharge, and combinations thereof, and the like.

In some embodiments, the cell can be, for example, embryonic stem cells, amniocytes, blastocysts, morulas, and zygotes; leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, cuboid, columnar, squamous keratinized, and squamous non-keratinized cells, and pericytes; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; or a combination thereof. In some embodiments, a single three dimensional gel microenvironment may comprise at least two different types of cells. In some embodiments, a single three dimensional gel microenvironment may comprise 3, 4, 5, 10, or more types of cells.

The various types of cells that are used herein are grown and cultured according to methods well known in the art. Generally, a cell culture medium contains a buffer, salts, energy source, amino acids (e.g., natural amino acids, non-natural amino acids, etc.), vitamins, and/or trace elements. Cell culture media may optionally contain a variety of other ingredients, including but not limited to, carbon sources (e.g., natural sugars, non-natural sugars, etc.), cofactors, lipids, sugars, nucleosides, animal-derived components, hydrolysates, hormones, growth factors, surfactants, indicators, minerals, activators of specific enzymes, activators inhibitors of specific enzymes, enzymes, organics, and/or small molecule metabolites.

Some embodiments may comprise growth and differentiation factors including, but not limited to Acidic fibroblast growth factor, Adrenomedullin, Angiopoietin, Autocrine motility factor, Basic fibroblast growth factor, Bone morphogenetic proteins, Brain-derived neurotrophic factor, Cartilage-derived growth factor, Epidermal growth factor, erythropoietin, Fibroblast growth factor, Glial cell line-derived neurotrophic factor, Granulocyte colony-stimulating factor, Granulocyte macrophage colony-stimulating factor, Growth differentiation factor-9, Healing factor, Hepatocyte growth factor, Hepatoma-derived growth factor, Insulin-like growth factor, Keratinocyte growth factor, Migration-stimulating factor, Myostatin, Nerve growth factor (NGF) and other neurotrophins, Platelet-derived growth factor, Thrombopoietin, Transforming growth factor alpha, Transforming growth factor beta, Tumor necrosis factor-alpha, Vascular endothelial growth factor, placental growth factor, Bovine Somatotrophin, IL-1, IL-2, IL-3, IL-4-, IL-5, IL-6 and IL-7, or combinations thereof.

In some embodiments, the cell is selected from a group consisting of a normal cell, benign cell, cancer cell, immortalized cell, genetically engineered cell, stem cell and patient derived cells or a combination thereof. In a specific embodiment, the cell is a cancer cell.

In other aspects, various research important cells which can be encapsulated within the three dimensional gel microenvironment according to the present disclosure include, but are not limited to, Chinese hamster ovary (CHO) cells, HeLa cells, Madin-Darby canine kidney (MDCK) cells, baby hamster kidney (BHK cells), NS0 cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

In some embodiments, the cells in the three dimensional gel microenvironment can be examined for various cellular effects or changes. For example, a cellular effect can be, but not limited to cell growth, proliferation, inhibition of cell growth proliferation, differentiation or de-differentiation, cell death, cell survival, necrosis or inhibition of necrosis, cell-cell interaction, release of a cellular factor, transmitter or agent, release or uptake of an ion, change in cell adhesion, morphology or migration, or a change in an intracellular or extracellular signaling pathway, or a combination thereof.

Detection of the cells or cellular changes can be accomplished through various biochemical or biophysical means that are available to person of ordinary skill in the art. In some embodiments, the gel composition allows various compounds, metabolites, proteins, macromolecules or other substances of interest to diffuse into, through and out of the gel composition environment to study cellular changes or other biological properties of the cell of interest.

In some embodiments, detectable substances may be useful, for example, in viewing or examining the cells (e.g. as used in microscopy, fluorescence microscopy, flow cytometry). Examples of detectable substances include various enzymes, prosthetic groups, fluorescent materials, luminescent materials, dyes, bioluminescent materials, radioactive nuclides, positron emitting metals (for use in positron emission tomography), and nonradioactive paramagnetic metal ions. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$.

Other methods to examine cells include isolation of various biological molecules including deoxyribonucleic acid, ribonucleic acid, proteins, carbohydrates, lipids, metabolites or other organic or synthetic molecules, or any combination thereof. Other detections may include, but not limited to PCR, RT-PCR, ELISA assays, in situ hybridization, microarrays (e.g. proteomic, genomic, cDNA etc.) or other methods available to a person of ordinary skill in the art.

The present disclosure also provides for a method of testing the efficacy of chemotherapeutic agents on cancer cells encapsulated within a gel. The method generally comprises contacting a gel composition as described herein having an encapsulated cell or cancer cell therein with a chemotherapeutic agent and observing a cellular effect of the chemotherapeutic agent on the cell. The method further comprises acquiring a first measurement of the cellular effect on the cell prior to contacting the chemotherapeutic agent, followed by comparing the first measurement of the cellular effect to a second measurement of the cellular effect after contacting the chemotherapeutic agent. The method also includes measuring multiple cellular effects of the chemotherapeutic agent on a cancer cell.

The method may also include testing multiple chemotherapeutic agents at one time, sequentially, or in overlapping time periods. The method may also include multiple cell types encapsulated within the three dimensional gel microenvironment such as, but not limited to anchorage dependent or anchorage independent cancer types or any other type of cell listed herein, which are then subjected to a chemotherapeutic agent. Moreover, the cancer cells, or other diseased cells can be encapsulated with other types of cells as listed above.

A cancer or cancer cells refers a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream.

Cancer or cancer cells can include, but are not limited to carcinomas, sarcomas, lymphomas and leukemias, germ cell cancers, and blastomas which include but are not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplasia syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenstrom's macroglobulinemia, Wilms' Tumor, and women's cancers.

In some embodiments, the cancer or cancer cell is a hematological cancer. These cancers, also known as blood cancers, are a group of diverse cancers originated from bone marrow or lymphatic tissues, affecting blood functions. Hematological cancers include, for example, lymphoma, leukemia, myeloma or a lymphoid cancer, as well as a cancer of the spleen and the lymph nodes. Exemplary lymphomas include both B cell lymphomas and T cell lymphomas. B-cell lymphomas include both Hodgkin's lymphomas and most non-Hodgkins lymphomas. Non-limiting examples of B cell lymphomas include diffuse large B-cell lymphoma (DLBCL), follicular lymphoma (FL), mucosa-associated lymphatic tissue lymphoma (MALT), small cell lymphocytic lymphoma (overlaps with chronic lymphocytic leukemia), mantle cell lymphoma (MCL), Burkitt's lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia (CLL; also called chronic lymphoid leukemia), acute myelogenous leukemia (AML; also called acute lymphoid leukemia), chronic myelogenous leukemia (CML), B-cell prolymphocytic leukemia (B-PLL), acute lymphoblastic leukemia (ALL) and myelodysplasia (MDS). Hematological malignancies further include myelomas, such as, but not limited to, multiple myeloma (MM) and smoldering multiple myeloma (SMM). Other hematological and/or B cell- or T-cell-associated cancers are encompassed by the term hematological cancer. For example, hematological cancers also include cancers of additional hematopoietic cells, including dendritic cells, platelets, erythrocytes, natural killer cells, and polymorphonuclear leukocytes, e.g., basophils, eosinophils, neutrophils and monocytes. In some embodiments, the hematological cancer cell is a myeloma or lymphoma or a combination thereof. In other embodiments, the hematological cancer is lymphoma that is either a T-cell Non-Hodgkin Lymphoma or a B-cell Non-Hodgkin Lymphoma, or a combination thereof as described in further detail below.

Non-Hodgkin lymphomas (NHL) are a heterogeneous group of lymphoproliferative disorders of B and T cell origin that are treated with chemotherapy drugs with variable success rate that has only minimally increased over the past decades. Accordingly, there is a clear need for more specific and less toxic treatments.

One approach is the use of epigenetic drugs that target transcriptional complexes and DNA methylation, by reprogramming cells to a more chemosensitive phenotype. The paucity in translating these drugs to patients is, in part, due to the lack of adequate models to accurately and efficiently identify candidates and to build therapeutic schedules. For instance, there are no cell line models of follicular lymphoma or most non-cutaneous T-NHLs. Therefore, the treatment for these diseases is empirically translated from diffuse large B cell lymphomas, with much poorer outcomes and correlations to the patient's tumor. There is a need to develop three-dimensional systems that mimic the NHL microenvironment. One objective is to develop an artificial three-dimensional extracellular matrix (ECM) that will support the survival and growth of patient-derived primary B and T-NHL cells, possesses design flexibility, and be suitable for screening of anti-neoplastic reprogramming drugs. The present disclosure addresses this need.

The present gel compositions can provide a suitable three-dimensional microenvironment for growth and proliferation of lymphomas such as NHL. Lymphomas grow in presence of supporting cells such as follicular dendritic cells. Studies have been conducted using both types of cells to understand how the embodiments disclosed herein affect cellular growth and other processes. Initial observations suggest that with increasing percentages of gel components, the encapsulation efficiency of these cells goes down and in general encapsulated cells form near uniform clusters (this is a different characteristic of dendritic cells, as opposed to fibroblast cells that favor spreading).

In may also be advantageous to encapsulate these or other types of cancers and their supporting cells in gel systems that comprise multiple layers as described previously. In this way, the layers may more closely mimic the tissue where these cells are normally found. For instance, one layer may comprise the support cells, while another layer may comprise the cancerous cells, while still a further layer may comprise vascular cells. The different layers can communicate through physical or secreted signals or a combination thereof.

Further data suggests that αvβ3 is a pro-survival and chemoresistance factor for 8 human T-NHL cells representing the spectrum of immature and peripheral T-NHLs. Moreover, using 30 DLBCL lines, 9 T-NHL lines, and primary NHL cells obtained from patients in an ongoing Phase I clinical trial, it was established that epigenetic drugs like the RGD ligand binding integrin inhibitors of DNA Methyltransferase (DNMT) can specifically kill primary human DLBCL cells. Accordingly, the three dimensional gel culture systems proposed herein, further comprising integrin specificities which signal for pro-survival factors in primary NHL and supporting stromal cells, facilitate matrix network remodeling, and enhance diffusion of drugs such as chemotherapeutics and bioactive agents.

A "chemotherapeutic agent" as used herein is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), leflunomide (Arava®, Sanofi Aventis, CAS No 75706-12-6) trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(I,2-diphenylbut-I-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SUI 1248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOS AR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CBI-TMI); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-I I; topoisomerase inhibitor RFS 2000; difluoromethylornithine (DFMO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LYI 17018, onapristone, and FARESTON® (toremifme citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rlL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies including monoclonal antibodies and other specific agents such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idee), pertuzumab (OMNITARG™, 2C4, Genentech), trastuzumab (HERCEPTIN®, Genentech), tositumomab (Bexxar, Corixia), and gemtuzumab ozogamicin (MYLOTARG®, Wyeth).

In other embodiments, the chemotherapeutic agent used to contact a cancer cell can include, or be separate from a bioactive agent. Bioactive agents can include, but are not limited to, polynucleotides, polypeptides, polysaccharides, organic and inorganic small molecules. The term "bioactive agent" encompasses both naturally occurring and synthetic bioactive agents.

Bioactive agents can further be a drug, including, but not limited to, antimicrobials, antibiotics, antimycobacterials, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, prostaglandins, interleukins, interferon, chemokines, general inhibitors of the allergic response, antihistamines, analgesics, narcotic antagonists, non-steroidal anti-inflammatory agents, steroidal anti-inflammatory agents, antioxidants, vaso-active agents, bone-active agents, antiarthritics, and diagnostic agents.

Further bioactive agents may include physiologically active polypeptides include various physiologically active peptides used for treating or preventing human diseases, which are exemplified by hormones, cytokines, enzymes, immunoglobulins, growth factors, transcription regulatory factors, coagulation factors, vaccines, structural proteins, ligand proteins or receptors, cell surface antigens and receptor antagonists, and derivatives and analogues thereof.

Definitions

One skilled in the art may refer to general reference texts for detailed descriptions of known techniques discussed herein or equivalent techniques. These texts include Current Protocols in Molecular Biology (Ausubel et. al, eds. John Wiley & Sons, N.Y. and supplements thereto), Current Protocols in Immunology (Coligan et al, eds., John Wiley St Sons, N.Y. and supplements thereto), Current Protocols in Pharmacology (Enna et al, eds. John Wiley & Sons, N.Y. and supplements thereto) and Remington: The Science and Practice of Pharmacy (Lippincott Williams & Wilicins, 2Vt edition (2005)), for example.

Definitions of common terms in molecular biology may be found, for example, in Benjamin Lewin, Genes VII, published by Oxford University Press, 2000 (ISBN 0I9879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341).

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

As used herein, the term "isolated" in the context of a peptide, polypeptide, fusion protein, antibody or antigen-binding antibody fragment refers to a peptide, polypeptide, fusion protein, antibody or antigen-binding antibody fragment which is substantially free of cellular material or contaminating proteins from the cell or tissue source from which it is derived or obtained, or substantially free of chemical precursors or other chemicals when chemically synthesized. The language "substantially free of cellular material or contaminating protein" includes preparations of a peptide, polypeptide, fusion protein, antibody or antigen-binding antibody fragment in which the peptide, polypeptide, fusion protein, antibody or antigen-binding antibody fragment is separated from cellular components of the cells from which it is isolated or recombinantly produced. Thus, a peptide, polypeptide, fusion protein, antibody or antigen-binding antibody fragment that is substantially free of cellular material or contaminating protein includes preparations of a peptide, polypeptide, fusion protein, antibody or antigen-binding antibody fragment having less than about 30%, about 20%, about 10%, or about 5% (by dry weight) of other protein. When the peptide, polypeptide, fusion protein, antibody or antigen-binding antibody fragment is recombinantly produced, it is also preferably substantially free of culture medium, i.e., culture medium represents less than about 20%, about 10%, or about 5% of the volume of the protein preparation. When the peptide, polypeptide, fusion protein, antibody or antigen-binding antibody fragment is produced by chemical synthesis, it is preferably substantially free of chemical precursors or other chemicals, i.e., it is separated from chemical precursors or other chemicals which are involved in the synthesis of the peptide, polypeptide, fusion protein, antibody or antigen-binding antibody fragment. Accordingly, such preparations of a peptide, polypeptide, fusion protein, antibody or antigen-binding antibody fragment have less than about 30%, about 20%, about 10%, about 5% (by dry weight) of chemical precursors or compounds other than the peptide, polypeptide, fusion protein, antibody The following Examples are intended to illustrate the above invention and should not be construed as to narrow its scope. One skilled in the art will readily recognize that the Examples suggest many other ways in which the invention could be practiced. It should be understood that numerous variations and modifications might be made while remaining within the scope of the invention.

EXAMPLE 1

Bioadhesive Gel Compositions and Methods of Use

Materials and Methods
Hydrogel Microfabrication
Polydimethylsiloxane (PDMS) microwell molds were fabricated as reported earlier using Sylgard 184 (Dow Corning, MI) The microwells were plasma treated in a Harrick Plasma Cleaner for two minutes to make the microwells hydrophilic. To obtain siliconized glass slides, Sigmacote™ was applied to glass slides, dried, and finally rinsed thoroughly in DI water (Labconco). PEG-MAL (20,000 Da, 99% functionalized) was purchased from Laysan Bio, Inc. and DTT was purchased from Life Technologies. Silicate nanoparticle (Laponite XLG) were obtained from Southern Clay Products, Inc. (Louisville, Ky.). Type-A porcine skin gelatin was obtained from Sigma Aldrich (Milwaukee, Wis.).

A 5% w/v mixture of synthetic silicate nanoparticle (NP) in deionized water was prepared and vortexed for 2 minutes. The mixture transitioned from cloudy to clear, indicating fully exfoliated nanoparticles. A 12.5% w/v mixture of gelatin in DMEM was prepared and heated to 37° C. until the gelatin dissolved. Stock solutions of 0.4% w/v DTT and 25% w/v PEG-MAL in DMEM medium were prepared and kept on ice until ready. It should be noted that gels referred to as 0% PEG essentially means they were composed of gelatin and silicate nanoparticles only. Other composite gels were engineered with 2.5 or 5% PEG-MAL macromer. To fabricate microgels, the precursor solutions were mixed to form two component mixtures (FIG. 1b). Component A consisted of gelatin, DTT, and DMEM. For cell-encapsulated gels, cell suspension was added to Component A. Likewise, Component B consisted of PEG-MAL, silicate NP, and DMEM. To formulate bulk gels, the two component mixtures were simply mixed at pH 7.4 and heated to 37° C. for one hour. To prepare the microgels, a drop of Component A was placed on a plasma treated microwell mold. A small drop of Component B was placed on a siliconized glass slide, which was then aligned on top of the mold and allowed to diffuse through a thin layer of Component A. A 25 g weight was placed on top of the slide to remove any excess solution. After one minute the glass slide was removed and the mold with the microgel was placed in media. The siliconization prevented the hydrogel from adhering to the glass slide. Hydrogels were prepared according to the compositions in Table 1 and were cured in growth media conditions for an hour.

Silicate Nanoparticle Cytotoxicity Assay
The effect of silicate NP on the metabolic activity of human cells was determined using MTT assay (ATCC® 30-1010K) according to manufacturer's protocol. In brief, human mesenchymal stem cells were cultured in 96 well plates with density of 2000 cells/cm². The pre-seeded cells were subjected to different concentrations of nanoparticles (10 μg/mL to 10 mg/mL). After 24 h, media was removed and was replaced with 100 μL of fresh culture medium and 10 μL of MTT solution. 4 h post incubation, lysis buffer was added to each well and was allowed to incubate at 37° C. for 2 hours and absorbance was measured at 570 nm.

Hydrolytic Swelling/Degradation and Enzymatic Degradation
50 μL PEG-MAL hydrogels with or without gelatin and silicate NP were prepared in a 500 μL tube. After gelation, hydrogels were weighed and transferred to a 2 mL tubes. Each tube was filled with 200 μL of either PBS (pH 7.4) or 4 mg/mL collagenase IV solution (reconstituted in PBS) for hydrolytic or enzymatic degradation studies, respectively. These hydrogels were incubated at 37° C. on a slow speed rocker. Weight measurements were taken at 0, 8, 12, 24, 48, and 72 h for both hydrolytic and enzymatic degradation sets. Additional weight measurements were taken at 96, 120, 144, and 168 h for the hydrolytic degradation set. After each measurement, fresh PBS or collagenase solution was replenished into each respective tube. Swelling (weight) ratio of these hydrogels was determined using the following relation as reported earlier by us[45]:

$$Qm = \frac{\text{Weight } (t > 0)}{\text{Weight } (t = 0)}$$

Dry weight measurements were also performed to determine decrease in polymer mass with hydrogel degradation. 50 μL hydrogels were prepared for t=0 and 48 h for both hydrolytic and enzymatic degradation groups. The hydrolytic and enzymatic gels were soaked in PBS and 4 mg/mL collagenase IV solution respectively. All groups at t=0 were immediately dried in an oven at 60° C. and weighed. The t=48 h groups were dried and weighed after possible degradation after 48 h. The degradation was measured as a ratio between the initial dry weight and final dry weight.

Hydrogel Contraction Studies
For matrix contraction studies we used mouse embryonic fibroblast (MEF) cells stromal cell model. MEFs were typsinized, centrifuged, and re-suspended in DMEM at 2×10⁸ cells/mL. Cell-laden hydrogels with 5 μL total volume were prepared with 0, 50,000, and 100,000MEF cells. High cell densities were chosen to maximize contraction in the gels. As previously, Component A and Component B were combined and allowed to polymerize. Hydrogels were cured for 10 minutes before DMEM media was added into the well. Images of the whole gel were taken using an EVOS microscope (Life Technologies) at t=0, 24, 48, and 72 h. The area of the 2d projection of the gels were measured using ImageJ.

Rheology

250 µL hydrogels of various compositions were prepared in 500 µL Eppendorf tubes and incubated overnight in PBS at 4° C. Prior to rheology measurements using the Discovery Hybrid Rheometer from TA Instruments (New Castle, Del.), each gel was incubated at 37 ° C. for 5 minutes. The elastic and loss moduli were measured as a function of frequency that varies from 0.1 to 100 rad/s using 25 mm 2.021 degree cone-plate geometry.

Cytocompatibility and Spreading of Cancer Cells

Cervical cancer HeLa cells were typsinized, centrifuged, and re-suspended at a concentration of $2 \times 10^8$ cells/mL in DMEM with 10% FBS and 1% Penicillin/Streptomycin. 20 µL microgels with 400,000 encapsulated cells were prepared according to the procedure above. Separate sets of gels were made for t=0, 24, 48, and 72 hr for each studied composition. The gels were stained with Calcein-AM and Ethidium Homodimer-I and imaged using a Nikon TE 2000U florescence microscope. Live and dead cell counts as well as cell spreading measurements were performed using ImageJ. Briefly, both live and dead images were stacked in ImageJ and the stacked images were analyzed for Maxima function that determines the local maxima in a rectangular section of image (i.e. each well) and marks one cell per maximum. This tool counts the number of local maxima of brightness outside a given tolerance, or the number of "bright spots". For spreading, the images were preprocessed using a band-pass filter to reduce any noise. Area and circularity ([circularity]=$4\pi$ [area]/[perimeter]$^2$) measurements were performed using the analyze particles function in ImageJ. Samples were also imaged using confocal microscopy to determine the distribution of the cells.

Co-Encapsulation of Adhesive and Suspension cells

TF-1 a leukemia suspension cells and anchorage-dependent cervical cancer HeLa cells were co-encapsulated in microgels using the method described above. Molecular Probes® CellTracker™ fluorescent probes were used to study the co-encapsulation of these cells. TF-1a cells were re-suspended in RPMI media and stained with Cell Tracker™ CMTMR at 37° C. for 30 minutes. The cells were then centrifuged and re-suspended twice in DMEM to remove excess dye. Adherent HeLa cells were stained with CellTracker™ CMFDA at 37° C. for 30 minutes. A mixture of $1 \times 10^8$ TF-1a cells/mL and $5 \times 10^7$ HeLa cells/mL in DMEM was prepared. 20 µL micro gels encapsulated with 200,000 TF-1 a and 100,000 HeLa cells were prepared according to the procedure above. The gels were imaged on a Nikon TE 2000U florescent microscope at t=0, 24, and 48 hr.

Cell Proliferation and Metabolic Activity

For cell proliferation studies, cell numbers and volume was adjusted to fit within the linear range of the metabolic activity assay standard curve over the 6 day study. Three sets of cell combinations were tested: 5,000 HeLa cell, 5,000 TF-1a cells, and 5000 HeLa cells with 5,000 TF-1a cells. A set of microgels for each time point (t=0, 1, 3, and 6 days) was prepared and placed in a 96 well plate with 100 µL of RPMI medium. For control, bulk and microgels of the studied compositions were prepared without cells. At pre-determined time points, CellTiter 96® AQueous One Solution Cell Proliferation assay solution (Promega, 20 µL reagent/100 µL medium) was added to each well and incubated for 4 h at 37° C. and 5% CO2. The fluid was transferred to a new well plate and centrifuged. Supernatant was analyzed using a BioTek plate reader at 490 nm. Proliferation was evaluated using the fold increase in the measured absorbance.

Statistics

Analysis of variance (ANOVA) statistical analyses were performed using GraphPad Prism 9.1 software with Tukey's test for pairwise comparisons. For cell spreading analysis across Different time points, ANOVA was performed with Bonferroni correction. For studies involving effect of hydrogel mechanical properties on cell survival, ANOVA was performed with Tukey's correction. A p-value of less than 0.05 was considered significant. All studies were performed in triplicates unless otherwise noted. All values are reported as Mean±S.E.

Results and Discussion

Figure 2:
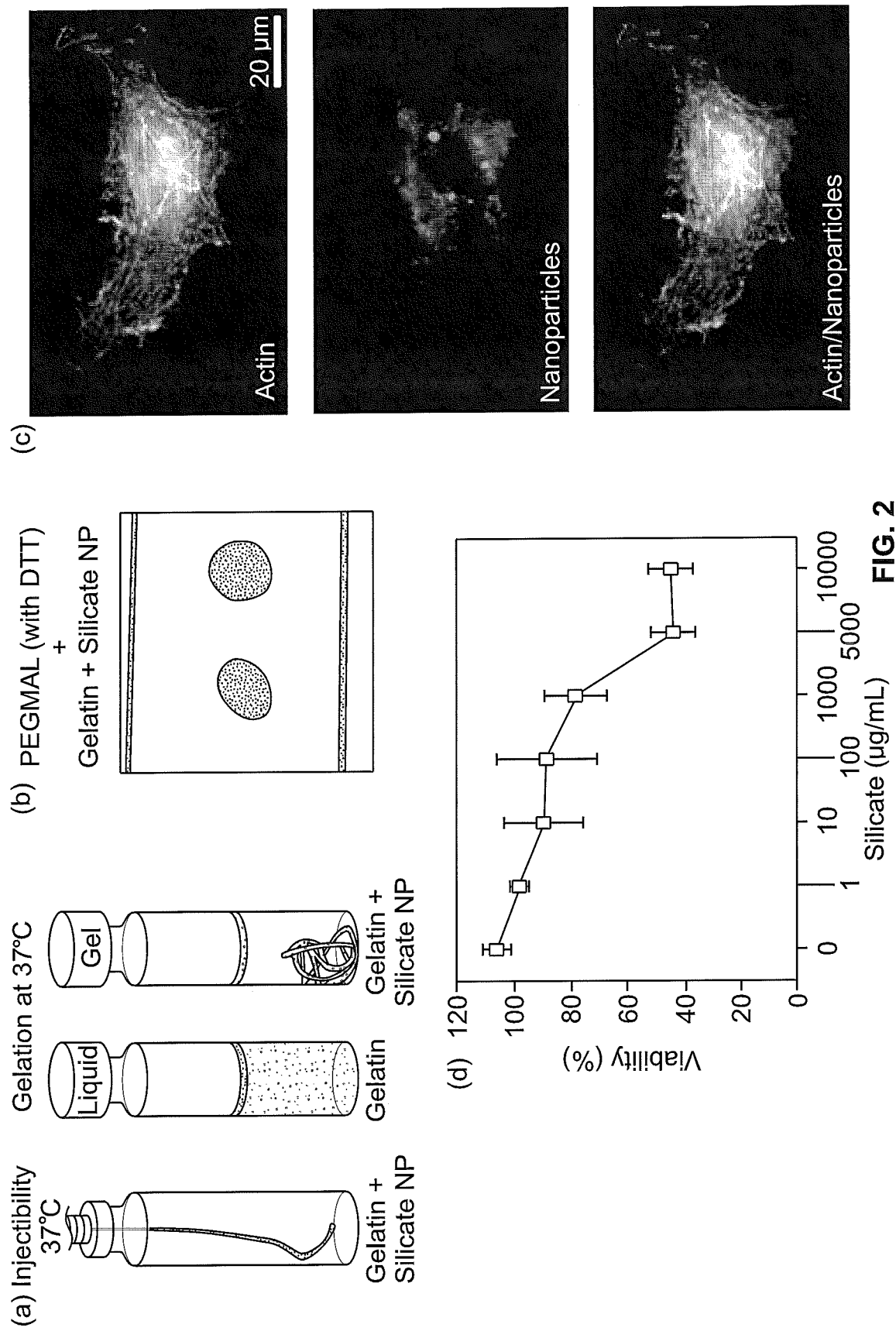
FIG. 2 illustrates Gelatin crosslinking with silicate nanoparticles. (2a) The image indicates the injectability and stability of gelatin at 37° C. in presence of NP while gelatin alone liquefies. (2b) The image indicates representative bulk gels formed with DTT cross-linked PEG-MAL with incorporated gelatin-silicate NPs. (2c) Confocal images of cellular uptake of silicate NP. (2d) Cell metabolic activity at increasing dose of silicate nanoparticles.

Approaches to fabricate cell encapsulated PEG-based microgels using Michael-type addition reaction have been few and arrays of bioadhesive PEG-MAL microgels with adhesive proteins and nanoparticles demonstrating cell encapsulation have not been reported. We have developed an array of bioadhesive PEG-MAL microgels using a simple microwell approach (FIG. 1b). These microgels present a cell supportive microenvironment with adhesivity and tunable swelling, mechanical, and degradation properties. We identified that addition of silicate NP in gelatin solution at 37° C. results in formation of a hydrogel that prevents liquefaction of gelatin at 37° C. (FIG. 2a). Polyampholytic gelatin, containing positively and negatively charged regions, strongly interacts with the anisotropically distributed opposite charges on the synthetic silicate NPs (20-30 nm in diameter and ~1 nm in thickness), as an outcome of which gelatin remains stable and does not liquefy at 37° C.

The adhesive protein-NP hydrogel, in this case, gelatin-NP hydrogel, was used as an adhesive interpenetrating network with a maleimide functionalized poly alkylene oxide (e.g. PEG-MAL) network cross-linked with DTT (FIG. 2b), which otherwise is non-adhesive in nature. Composite hydrogels and microgels of functionalized poly alkylene oxide (e.g. PEG-MAL) and adhesive protein-NP (e.g. gelatin-NP) were called interpenetrating networks. Adhesive proteins and silicate-NP hydrogels or microgels without any PEG-MAL (or other maleimide functionalized poly alkylene oxide) component or vice versa were not considered interpenetrating networks. The rationale for using DTT was that the di-thiols provide an easy and fast reacting cross-linker that is non-degradable and prevents any cell spreading if no other degradable matrix is present. Previous studies have demonstrated that DTT incorporated hydrogels with DTT concentrations up to 70 mM do not cause significant cytotoxicity. In our studies we used DTT at a maximum concentration of 4.5 mM. Another potential concern was the cytotoxicity of silicate nanoparticles. As indicated in FIG. 2c, the freely available nanoparticles were readily taken up by the human cells, indicating the cytocompatible behavior and maintained >80% cell viability up to 1000 µg/mL concentration (FIG. 2d). In our studies, the concentration of nanoparticles was below this threshold limit. Our results are in good correlation with previously reported findings by Gaharwar et aL that silicate nanoparticles are cytocompatible.

We explored the effect of network composition, presence and absence of gelatin-NPs within PEG-MAL networks on hydrolytic swelling and degradation. We compared bulk gel compositions consisting of 5% PEG-MAL and 2.5% PEG-MAL with varying weight percentages of gelatin-NP (FIGS. 3a and 3b). As expected for hydrogels containing no gelatin- NP, 5% PEG-MAL hydrogels swelled significantly more than 2.5% PEG-MAL ones (p<0.05), with swelling ratio (Qm) 3.17 and 1.5, respectively. This difference in swelling can be attributed to higher proportions of hydrophilic PEG in 5% gels compared to 2.5% PEG-MAL gels. Similarly, 2.5% PEG-MAL with gelatin-NP swelled significantly less than their 5% counterpart (p<0.05), irrespective of gelatin-NP percentages. Within the same w/v % of PEG-MAL, no significant difference in swelling ratio was observed with incorporation of gelatin-NP. Hydrogels containing only gelatin-NP showed significantly higher degradation than PEG containing gels, losing approximately half their weight within 48 h. These experiments were continued for 7 days with no significant change in normalized weight ratios compared to 48 h time point.

Previous studies have demonstrated that matrix metalloproteinase-mediated degradability of 3D cell culture is desirable because it allows for matrix remodeling, cell spreading, and migration within PEG-based networks. Since gelatin is prone to degradation in presence of proteases like collagenase secreted by cells, we assessed change in weight in bulk gels made of 2.5% PEG-MAL with varying weight % of gelatin-NP in presence and absence of enzyme. As indicated in FIG. 3b, with 2.5% PEG-MAL hydrogels modified with 0.5% gelatin and 0.3% NPs, we observed approximately two-fold increase in hydrogel weight when exposed to collagenase for 24 h compared to the gels not treated with collagenase (p<0.05). With 2.5% PEG-MAL hydrogels containing 2.5% gelatin and 1.5% NPs, the increase in weight ratio was only 1.2-fold (p>0.05) compared to untreated counterparts, which could be attributed to the presence of more number of silicate NPs preventing degradation and swelling. We anticipated this behavior because with degrading gelatin network, the cross-linked architecture would change causing an increase in absorption of aqueous media.

To determine decrease in polymer mass because of degradation, we performed dry weight measurements on the hydrogels over 48 h exposure to PBS or collagenase (FIG. 3c). With PBS, no significant change in dry mass was observed for PEG only gels and 2.5% PEG-MAL hydrogels containing 0.5% gelatin and 0.3% NPs. For hydrogels consisting only of gelatin-NPs and no PEG component (called 0% PEG), a significant 52% decrease in dry weight was observed over 48 h (p<0.05). This observation supports our hypothesis that the composite bioadhesive hydrogels of PEG-MAL with gelatin-NPs are more mechanically stable than the ones without PEG, under hydrolytic conditions.

With collagenase, a significant 30% decrease in dry weight was observed for PEG-MAL hydrogels with gelatin-NPs which could be attributed to degradation of gelatin component. In the absence of PEG, gelatin-NP gels showed significant 50% degradation in collagenase (p<0.05) compared to PEG only gels but was not significantly different than PEG-gelatin-NP composite gels. It should however be noted that all 0.5% gelatin with 0.3% NP hydrogels were unstable in absence of PEG and disintegrated into pieces demonstrating mechanical instability of these gels.

Figure 4:
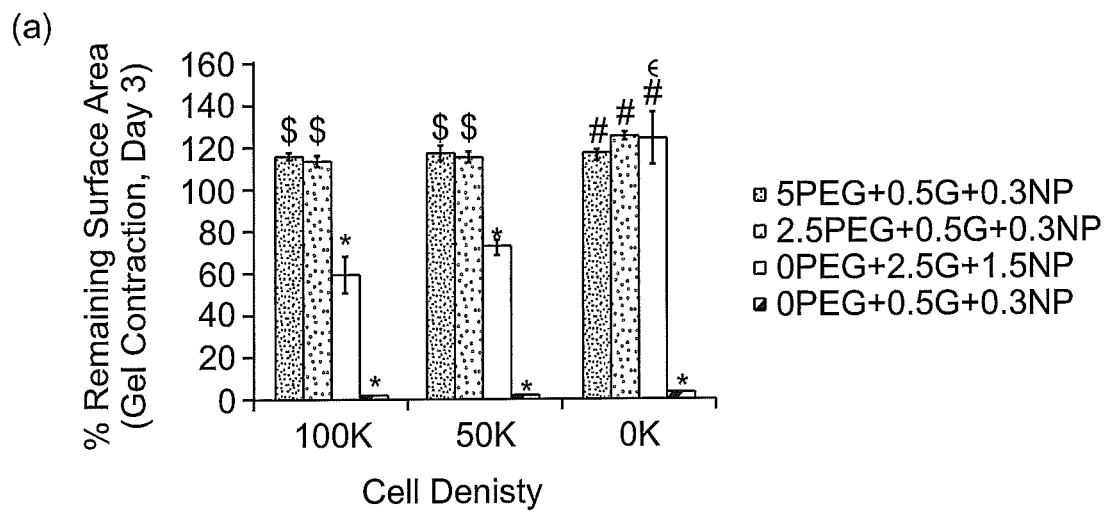
FIG. 4 illustrates the mechanical properties of composite hydrogels. (4a) Cell-mediated contraction of hydrogels. The gels were formed, on a 24 well tissue culture plate, from varying proportions of the stock solutions and indicated number of cells. Bar graph represents the percent of hydrogel bottom surface area remaining at day 3 (compared to day 0). *p<0.05 compared to all other groups at a particular cell density; $p<0.05 compared to gelatin-NP only gels at a particular cell density; #p<0.05 compared to 0.5 G+0.3 NP gels at a particular cell density; ∈p<0.05 for a group across different seeding density; n=3. (4b) The viscoelastic behavior of the PEG-MAL and PEG-MAL composite interpenetrating networks was studied by measuring the G' and G" moduli of the gels as a function of frequency.
Figure 4:
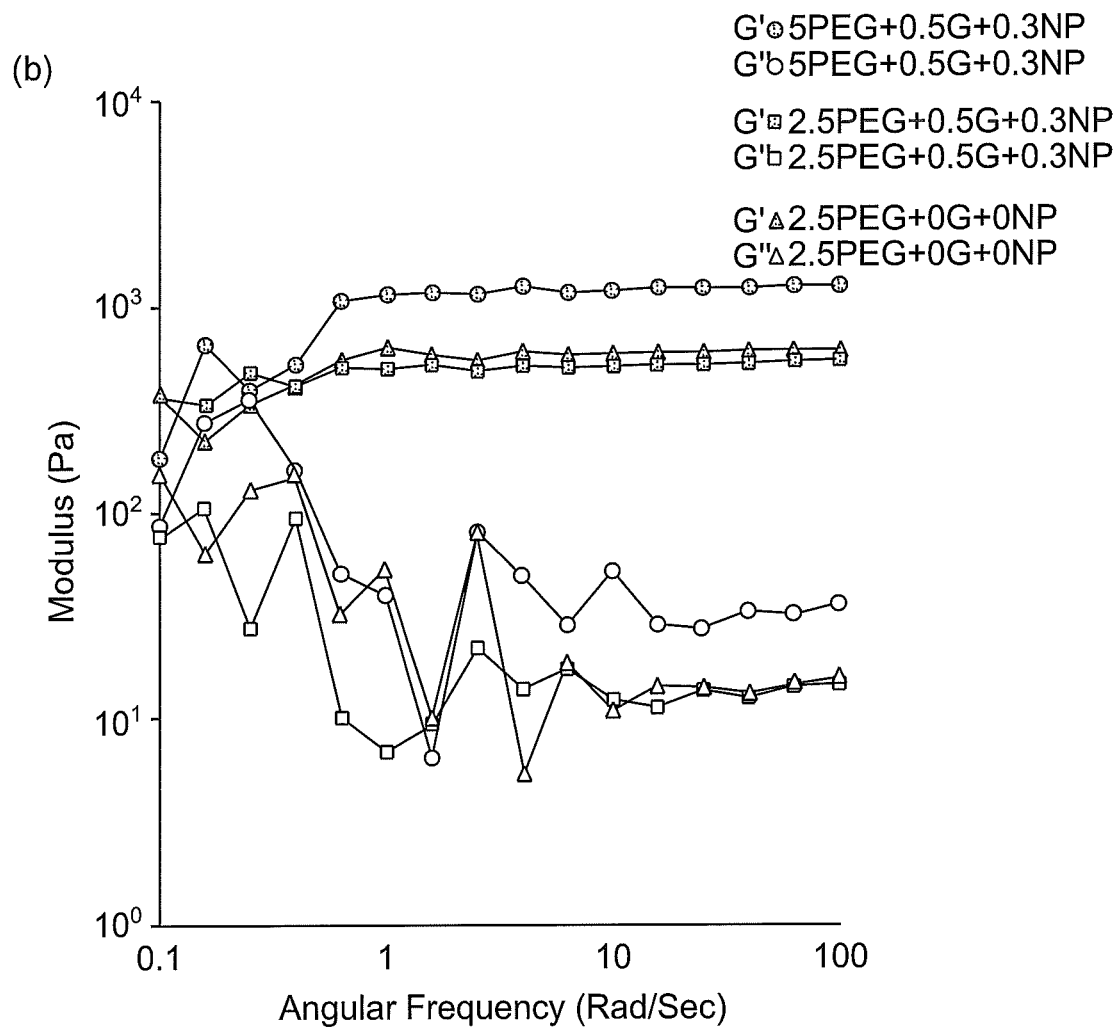

Previous studies by Swartz and colleagues have shown that culture of fibroblastic cells in 3D collagen-only matrices (2.5 mg/mL type I collagen) contracted the matrix to 20% of its original size within 72 h making long-term culture difficult. Since our goal is to establish a 3D-cell culture platform for long-term studies, we anticipated the gelatin-NP gels to contract upon cell encapsulation. Based on swelling studies, we expected the hydrogels to swell and the presence of cells to counteract such swelling. As indicated in FIG. 4a, 5% PEG-MAL with 0.5% gelatin and 0.3% NP and 2.5% PEG-MAL with 0.5% gelatin and 0.3% NP showed no significant gel contraction (p>0.05) for all cell counts compared to hydrogels with no cells. On the other hand, 2.5% gelatin and 1.5% NP with no PEG showed significant contraction at 50,000 and 100,000 cell seeding density (p<0.05). As discussed earlier, the 0.5% gelatin and 0.3% NP disintegrated into small pieces for all cell counts by day 3 independent of the cell count indicating mechanical instability of the bulk gels. These studies demonstrate that by incorporating minimal amount of gelatin-NPs, we can control the swelling ratio, degradation kinetics, as well as cell induced contraction of matrices.

We next examined the effect of gelatin-NP incorporation on stiffness of bulk PEG-MAL hydrogels. All rheological measurements were performed on swollen hydrogels equilibrated in PBS and the storage and loss moduli were plotted as a function of angular frequency (FIG. 4b). Rheological characterization of the adhesive and non-adhesive hydrogels was performed with similar PEG concentration to examine the effect of gelatin-NP incorporation on hydrogel stiffness. There was no difference in the storage modulus with incorporation of gelatin-NPs indicating that incorporation of adhesive components in the bulk PEG-MAL hydrogel does not affect its viscoelastic properties. Furthermore, the storage moduli of 5% PEG hydrogels were higher than the 2.5% PEG hydrogels for the same amount of adhesive ligands, indicating increased stiffness with increasing polymer concentration, independent of adhesive ligand incorporation.

The main aspect of this study was to transform the PEG-MAL-based adhesive gels into microgels. We next manufactured micron-scale hydrogels using a simple microwell technique. Microgels were prepared in a two-step process where Component A consisting of gelatin, DTT, and DMEM media (with cells if applicable) was poured onto the microfabricated PDMS wells (FIG. 1b). Typically 3-4 microwell constructs each carrying 500 wells were placed on a glass slide and Component B (PEG-MAL, silicate nanoparticle, and DMEM media) was slowly placed on top of each construct with Component A. After one minute the glass slide was gently removed and the mold with the microgels was submerged under growth media. All gels formed in <5 min, even at the lowest concentration of PEG-MAL and gelatin-NPs. We did not observe overlapping regions of polymer gel network between individual wells, except occasionally with gelatin-NP formulations only (particularly at higher w/v % of gelatin and NP).

To demonstrate the PEG-MAL (DTT) with gelatin-NPs as a cytocompatible interpenetrating microenvironment for cell encapsulation, cervical cancer HeLa cells were encapsulated in ECM mimetic hydrogels using the 5 or 2.5 w/v % PEG-MAL formulation with 0.5% gelatin and 0.3% NP or 2.5% gelatin with 1.5% NP. Following polymerization, the cervical cancer cell laden microgels were cultured under standard growth conditions, and cell viability was assessed at 24, 48 and 72 h using Live/Dead staining, which discriminates dead cells from viable cells based on membrane integrity (FIGS. 5a). We analyzed 16 wells per sample to determine percentage of live cells. Quantitative analysis of images obtained from fluorescence microscopy indicated excellent cell viability 84±1.7% after 24 h in microgels formed with interpenetrating networks of 5% PEG-MAL with 0.5% gelatin and 0.3% NPs, which however was significantly reduced to 75±1.7% after 72 h (FIG. 5b). On the other hand, bioadhesive microgels of 2.5% PEG-MAL with 0.5% gelatin and 0.3% NP composition indicated excellent 87±0.09% viability over 24 h and increased to 92±0.7% over 72 h. 5% and 2.5% PEG-MAL microgels with no gelatin and NPs demonstrated 89±1.1% and 87±1.3% viable cervical cancer cells respectively. After 72 h, these control PEG-MAL microgels without gelatin-NPs demonstrated only 62±1.2% viability with 5% PEG-MAL, and 78±1.4% with 2.5% PEG-MAL gels. Finally, microgels containing only 0.5% gelatin with 0.3% NP showed nearly 80% viability over 72 h. These differences in cell viability with PEG-based gels could be explained based on the differences observed in mechanical properties, degradability (allowing matrix remodeling), and cell spreading behavior as discussed in later sections. Confocal imaging further confirmed that the cells remain well distributed inside the hydrogel over 72 h (FIG. 5c).

Figure 6:
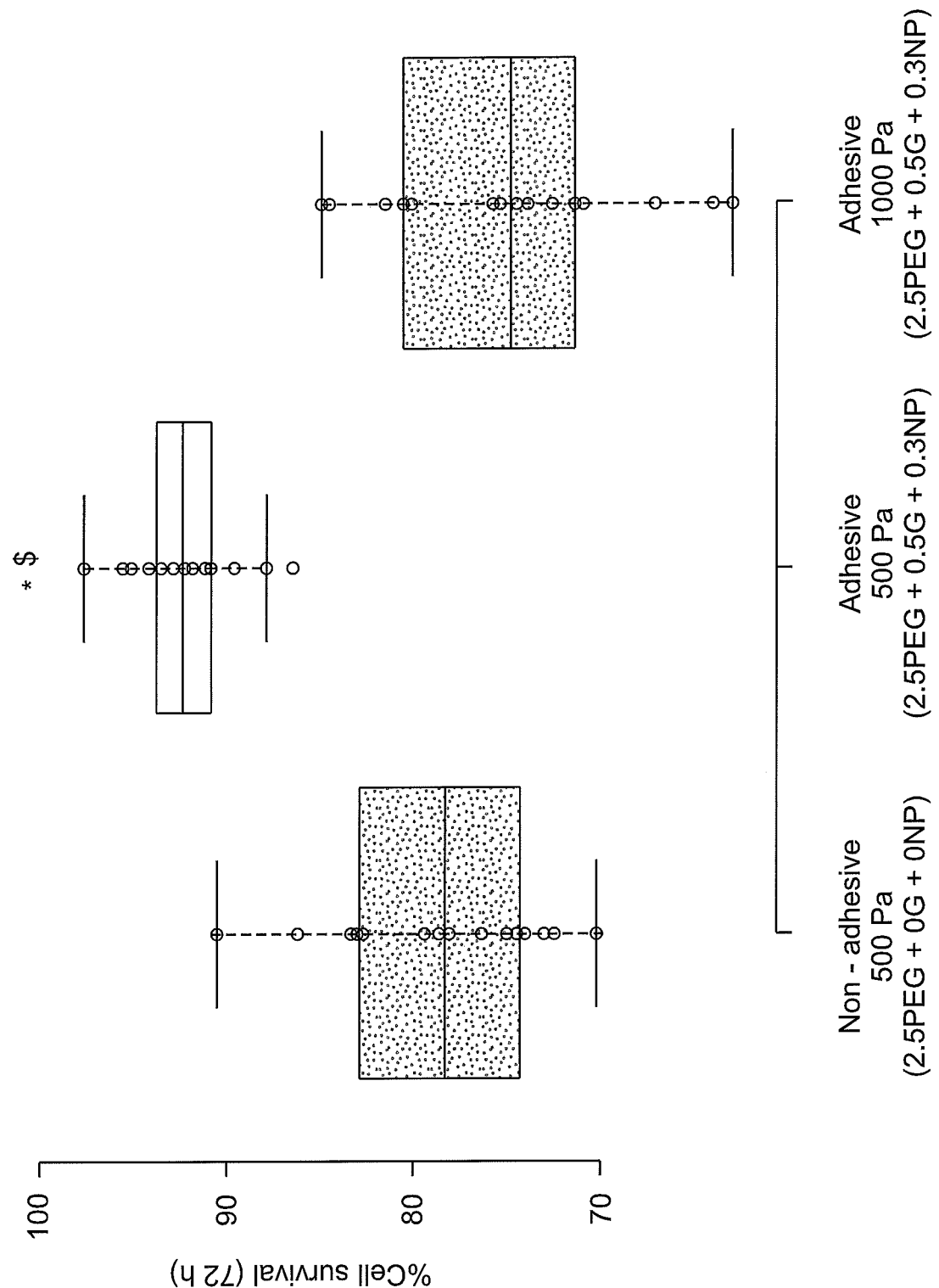
FIG. 6 illustrates the effect of microgel stiffness on cell survival. Box plot represents percent cell survival of HeLa cells after 72 h of culture in microgels with approximately 550 and 1100 Pa storage modulus, as determined from bulk gels analysis at 10 kHz frequency. n=16. * p<0.05 compared to non-adhesive hydrogels with same 500 Pa modulus; $p<0.05 compared to adhesive hydrogels with 1000 Pa modulus. All adhesive hydrogels were composed of equivalent amount of adhesive ligand.

Interestingly, when cultured in 2.5% PEG-MAL microgels with same mechanical strength (based on bulk gel analysis), cell survival significantly increased with incorporation of adhesive ligand (FIG. 6). When the ligand density was kept same (0.5% gelatin with 0.3% NP), increase in hydrogel stiffness from 550 Pa to 1100 Pa with increasing PEG % resulted in significant reduction in cell survival. The enhanced survival in 2.5% PEG gels with adhesive ligands is attributed to integrin mediated cell adhesion and lower crosslinking density of the polymer compared to 5% PEG gels. These finding are further supported by our observations that 5% PEG-MAL gels with no adhesive ligand showed significantly lower cell survival than 5% PEG-MAL with adhesive components. Therefore, these composite microgels could be used to study independent effect of stiffness and ligand density on cell survival and functioning.

We next evaluated the effect of bioadhesive microgels on cell spreading by measuring the average cell area and average circularity of micro-encapsulated HeLa cells (FIG. 7a). As mentioned earlier, one of the rationale for using DTT as a cross-linker was to prevent any matrix-degradation mediated spreading of cells. At t=0, the encapsulated cells were spherical in shape. At t=48 h, we did not observe any spreading in PEG-MAL microgel (p>0.05) and marginal spreading in 0.5% gelatin with 0.3% NPs microgels (no PEG-MAL, p>0.05) compared to their respective day 0 average cell spreading areas (FIG. 7b). Notably, it was only the microgels formed with 2.5% PEG-MAL with 0.5% gelatin and 0.3% NP that showed significant spreading (p<0.05) compared to day 0 cells in the same microgels and compared to all other groups at day 2. Importantly, when compared across all formulations, microgels made of 2.5% PEG-MAL with 0.5% gelatin and 0.3% NP clearly demonstrated a superior microenvironment that supported cell spreading and survival. Cell spreading is supported by favorable mechanical properties, bioadhesivity, and enzymatic degradability of gelatin components allowing niche remodeling. We further evaluated the circularity of these cells with lower circularity indicative of cell spreading. As indicated in FIG. 7c, microgels made of 2.5% PEG-MAL with 0.5% gelatin with 0.3% NP demonstrated significantly lower (p<0.05) average cell circularity values further confirming that this particular compositions supports cell spreading. These results clearly demonstrate the significant effect of gelatin incorporation and hydrogel remodeling on HeLa cell spreading and survival. This spreading behavior is not unique to HeLa cancer cells and we observed similar spreading behavior with encapsulated mouse embryonic fibroblasts suggesting the cell supportive microenvironment could support other anchorage-dependent cell types.

The final aspect of this study was to explore the potential of PEG-MAL hydrogels with gelatin-NPs for co-encapsulation of suspension and anchorage dependent cells. Such co-culture supportive microenvironments are relevant for bone-marrow and lymphoid tissues. For proof of concept, we co-encapsulated TF-1a leukemia suspension cells and anchorage-dependent HeLa cervical cancer cells that could possibly mimic the rare occurrence of cervical cancer in patients with leukemia. Co-encapsulation results (FIG. 8a) clearly indicate successful encapsulation of both cell types with uniform distribution. These cells were viable over 48 h and in some samples we observed HeLa cell spreading at day 2. Similar to our previous observations, 2.5% PEG-MAL with gelatin-NP outperformed other groups. We finally assessed whether the encapsulated cells in co-culture were metabolically active and proliferative compared to individual cell cultures. As indicated in FIG. 8b, all three cell cultures demonstrated significantly (p<0.05) higher proliferation rate over a week in bioadhesive microgels as compared to non-adhesive PEG-MAL only gels (cross-linked with DTT) or PEG-MAL with gelatin but no silicate NP (preventing gelation of gelatin at 37° C.). Taken together, these studies demonstrate the feasibility to co-encapsulate suspension and anchorage-dependent cells together in a growth supportive microenvironment where the both cell types remain metabolically active.

Conclusion

In summary, this study presents a facile approach to micromanufacture arrays of bio-adhesive PEG-MAL microgels using Michael-type addition reaction and interpenetrating networks of adhesive protein, gelatin, such that gelatin remains stable and provides a cell supportive microenvironment under normal cell culture conditions. The ease of fabrication, cytocompatible reaction conditions, tunable swelling, enzymatic degradation, and mechanical properties render this microgel platform novel and useful for a wide range of cell and tissue engineering applications. Use of 4-arm PEG-MAL could further allows for conjugate addition of thiolated growth factors to one of the PEG arms to engineer cell-instructive matrices for controlled cell programming as well as differentiation. Silicate nanoparticles have been shown to preferentially induce osteogenic differentiation of human mesenchymal stem cells, therefore, such matrices will also provide suitable 3D niches for stem cell differentiation.

TABLE 1

Hydrogel compositions. These hydrogel compositions were examined in the various experiments performed in this study. They are referred to by the names given in the first column.

| COMPOSITION | PEG-MAL (W/V %) | DTT (W/V %) | GELATIN (W/V %) | SILICATE NP (W/V %) |
|---|---|---|---|---|
| 5PEG + 2.5G + 1.5NP | 5 | 0.07 | 2.5 | 1.5 |
| 5PEG + 0.5G + 0.3NP | 5 | 0.07 | 0.5 | 0.3 |
| 5PEG + 0G + 0NP | 5 | 0.07 | 0 | 0 |
| 2.5PEG + 2.5G + 1.5NP | 2.5 | 0.03 | 2.5 | 1.5 |
| 2.5PEG + 0.5G + 0.3NP | 2.5 | 0.03 | 0.5 | 0.3 |
| 2.5PEG + 0G + 0NP | 2.5 | 0.03 | 0 | 0 |
| 0PEG + 2.5G + 1.5NP | 0 | 0 | 2 | 1.5 |
| 0PEG + 0.5G + 0.3NP | 0 | 0 | 0.5 | 0.3 |

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A composition comprising:
a first network comprising a maleimide-functionalized poly alkylene oxide cross-linked with a linking agent and
a second network comprising an adhesive protein complexed with an ionically charged nanoparticle which is separate from the first network, wherein the separate first and second networks diffuse and mix together so that the second network interpenetrates into, and is incorporated within, the first network, wherein said adhesive protein comprises gelatin or collagen.

2. The composition of claim 1, wherein said adhesive protein is gelatin.

3. The composition of claim 1, wherein said linking agent is dithiothreitol.

4. The composition of claim 1, wherein said nanoparticle is a silicate nanoparticle.

5. The composition of claim 1, wherein said maleimide-functionalized poly alkylene oxide is maleimide-functionalized polyethylene glycol.

6. The composition of claim 1 further comprises a cell.

7. The composition of claim 6, wherein said cell comprises a cancer cell.

8. The composition of claim 1, wherein said composition comprises a plurality of layers.

9. The composition of claim 8, wherein said plurality of layers are identical or not identical.

10. The composition of claim 8, wherein said plurality of layers comprises separate layers.

11. The composition of claim 1, wherein said composition is a hydrogel or microgel.

12. The composition of claim 11, wherein said microgel is fabricated into a microarray.

13. The composition of claim 1, wherein said maleimide-functionalized poly alkylene oxide is present in a concentration of from 0.1% to 2.5% by weight.

14. The composition of claim 1, wherein said adhesive protein is present in a concentration of from 0.1% to 0.5% by weight.

15. The composition of claim 1, wherein said ionically charged nanoparticle is a silicate nanoparticle present in a concentration of from 0.1% to 0.3% by weight.

* * * * *